US007122561B2

(12) United States Patent
Raman et al.

(10) Patent No.: US 7,122,561 B2
(45) Date of Patent: Oct. 17, 2006

(54) TREATMENT OF SKIN CONDITIONS

(75) Inventors: Amala Raman, London (GB); Zhixiu Lin, London (GB); Robert C. Hider, Essex (GB); Radhakrishnan Venkatasamy, London (GB)

(73) Assignee: BTG International Limited, London (GB)

( * ) Notice: Subject to any disclaimer, the term of this patent is extended or adjusted under 35 U.S.C. 154(b) by 247 days.

(21) Appl. No.: 10/630,901

(22) Filed: Jul. 31, 2003

(65) Prior Publication Data

US 2004/0061142 A1 Apr. 1, 2004

Related U.S. Application Data

(62) Division of application No. 10/051,173, filed on Jan. 22, 2002, now Pat. No. 6,680,391.

(30) Foreign Application Priority Data

Jul. 13, 1998 (GB) ............................................. 9815177

(51) Int. Cl.
 A61K 31/445 (2006.01)
 C07D 317/44 (2006.01)
 C07D 307/00 (2006.01)

(52) U.S. Cl. ........................ 514/321; 514/317; 514/543; 549/441; 549/440; 549/430; 549/429

(58) Field of Classification Search ................. 514/321, 514/317, 543; 549/441, 440, 430
See application file for complete search history.

(56) References Cited

U.S. PATENT DOCUMENTS 4,209,445 A * 6/1980 Oediger et al. ............. 540/596
4,209,446 A * 6/1980 Schulze et al. ............. 540/596

FOREIGN PATENT DOCUMENTS

| DE | 27 57 483 B1 | 6/1979 |
| EP | 0 650 728 A1 | 5/1995 |
| JP | 6-336417 A1 | 12/1994 |
| JP | 10130203 | 5/1998 |
| WO | WO 96/25939 | 8/1996 |
| WO | WO 00/02544 | 1/2000 |

OTHER PUBLICATIONS

Chandhoke et al., "Interactive activity of Various species of piperidine . . . ", Database CAPLUS, AN 1978:573794, (abstract only), Indian Journal of Pharmaceutical Sciences, 1978, vol. 40(4), pp. 113–116.*
Banerji et al., "Sylvatine, New alkaide from *Piper sylvaticum*", Database CAPLUS, AN1973:442108(abstract only), Tetrahedron, 1973, vol. 29(7), pp. 977–979.*
Gaind, K.N. et al; "Preservatives LX"; Database CA Online; *Chemical Abstracts Service*; Columbus, Ohio, US; retrieved from STN, Database Accession No. 83:72580, 1983.
De Paula, Vanderlucia F. et al; "Synthesis and insecticidal activity of a new amide derivatives of perine"; *Pest Management Science*; 56(2), pp. 168–174 (2000).
Bennett, D.C.; Cooper, P.; Hart , I.; (1987) A line of non–tumourigenic mouse melanocytes, syngeneic with the B16 melanoma and requiring a tumour promoter for growth, International Journal of Cancer 39, 414–418.
Donato, S.; Kesavan, M.; Austin, S.; Mohan, K., and Rajagopalan, K.; (1990) Clinical trial of certain Ayurvedic medicines indicated in vitiligo, Ancient Sci. Life 9, 202–206.
Leung, A.Y.; (1985) Chinese Herbal Remedies, Publ. Wildwood House, London, UK, pp. 120–123.
Duke, J.A., and Ayensu, E.S. (1985) Medicinal Plants of China, vol. 2 Publ. Reference Publications Inc. Algonac, MI, USA, pp. 483–485.
Johri, R.K. and Zutshi U. (1992) An Ayurvedic formulation 'Trikatu' and its constituents, J. Ethnopharmacology 37, pp. 85–91.
Dymock W.; Warden, C.J. and Hooper, D. (1890) Pharmacographia Indica. Ed. Dymock W. Publ. K. Paul, Trench and Trubner, London, UK, pp. 166–181.
Kapoor, L.D. (1990) Handbook of Ayurvedic Medicinal Plants, Publ. CRC Press, Boca Raton, FL, USA, pp. 264–266.
The Wealth of India (1969), vol. VIII: Ph–Re. Publ. Publications and information directorate, CSIR, New Delhi, India, pp. 99–118.
Moss VNS (1953) Ayurvedic Flora Indica. Publ. not known, pp. 102–105.
Dutt, U.C. (1989) The Materia Medica of the Hindus, with a glossary of Indian Plants by KBL Sen and K.A. Sen, $2^{nd}$ Edition, Publ. Mittal, Dehlhi, India, pp. 241–244.
Dash, V.B. (1983) A Handbook of Ayurveda. Publ. Concept Publishing, pp. 93–97.
Oriowo, M.A. (1982) Anti–inflammatory activity of piperonyl–4–acrylic isobutyl amide, Plant Medica 44, pp. 54–56.
Kirtikar, K.R. and Basu, B.D. (1935) Indian Medicinal Plants, $2^{nd}$ edition, Eds. E. Blatter, J.F. Caius and K.S. Mhaskar, Publ. Lalit Mohan Basu, Allahabad, India, pp. 2128–2130 and 2133–2135.
Raman, A. and Lin, Z. (1996) ACTIVE Ingredients Conference Proceedings, Le Palais des Congres de Paris, France Nov. 13–14, 1996, Publ. Verlag fuer Chemische Industrie H. Ziolkowsky GmbH Augsburg, Germany, pp. 203–221.
Nadkarni, A.K. (1976) Dr. K.M. Nadkarni's Indian Materia Medica, vol. 1, Publ. Popular Parkashan, Bombay, India, pp. 960–972 and 1267–1270.

(Continued)

*Primary Examiner*—Vickie Kim
(74) *Attorney, Agent, or Firm*—Nixon & Vanderhye

(57) ABSTRACT

The present invention provides piperine and analogues or derivatives thereof for the treatment of skin conditions treatable by stimulation of melanocyte proliferation, such as vitiligo, and also for treating skin cancer. The piperine and analogues or derivatives thereof may also be used to cosmetically promote or enhance the natural coloration of the skin.

13 Claims, 8 Drawing Sheets

OTHER PUBLICATIONS

Parmar, V.S.; Jain, S.C.; Bisht, K.S. et al. (1997), Phytochemistry of the genus *Piper* (Review), Phytochemistry 46, pp 597–673.

Weatherall, D.J.; Ledingham, J.G.G; Warrell, D.A., eds (1996), Oxford Textbook of Medicine, $3^{rd}$ edition Publ. Oxford University Press, Oxford, Section 23, pp. 3755–3759.

Raman, A.; Lin, Z.; Hoult, J.R.S., Identification of a phytochemical stimulant for the proliferation of mouse melanocytes in culture, J. Pharm. Pharmacol. 50 (Supplement), p. 247, 1998.

Lin, Z.; Donatein, P.; Raman, A.; Bennett, D.C. (1998) A naturally occurring growth promoter for human melanoblasts in culture J. Pharm. Pharmacol. 50 (Supplement), p. 218.

Lin, Z.; Hoult, J.R.S.; Bennett, D.C.; Raman, A. (1999) Stimulation of mouse melanocyte proliferation by *Pipernigrum L.* fruit extract and its main alkaloid, piperine, Planta Medica 65, pp. 600–603.

WPI Abstract Accession N° 97 061723/06; Chemical Abstracts Accession N° 126: 94788, Derwent Abstract JP08310949 (YAKULT) Nov. 26, 1996 & JAPIO Abstract.

WPI Abstract Accession N° 96–318931/32; Derwent Abstract JP08143562 (CADILA) Jun. 4, 1996 & JAPIO Astract.

Raman, A.; Lin, Z. and Hoult, J.R.S. (1998), Identification of a phytochemical stimulant for the proliferation of mouse melanocytes in culture, Poster displayed at $135^{th}$ British Pharmaceutical Conference, Eastbourne, U.K., Sep. 8–11, 1998.

Lin, Z.; Donatien, P.; Raman, A. and Bennett, D.C. (1998) Piperine, a naturally occurring growth promoter for human melanoblasts in culture, Poster displayed at $135^{th}$ British Pharmaceutical Conference, Eastbourne, U.K., Sep. 8–11, 1998; and at $39^{th}$ Annual Meeting of the American Society of Pharmacognosy, Orlando, Jul. 19–24, 1998.

A. Raman, Z. Lin and J.R.S. Hoult, A mouse melanocyte proliferation stimulation from *Piper nigrum L.*, "2000 Years of Natural Product Research—Past, Present, Future", Post displayed at Joint meeting of the American Society of Pharmacognosy, Association Francaise pour L'Enseignement et La Recherche en Pharmacognoise, Gesellschaft fuer Arzneipflanzenforschung and the Phytochemical Society of Europe, Amsterdam, The Netherlands, Jul. 26–30, 1999.

Lin, Z.X., Hoult, J.R.S., Raman, A. (1999) Sulphorhodamine B assay for measuring proliferation of a pigmented melanocyte cell line . . ., J. Ethnopharmacololgy 66, pp. 141–150.

* cited by examiner

TREATMENT OF SKIN CONDITIONS

REFERENCE TO RELATED APPLICATION

This application is a Divisional of application Ser. No. 10/051,173, filed Jan. 22, 2002, now U.S. Pat. No. 6,680,391, the entire content of which is hereby incorporated by reference in this application.

This application is a continuation-in-part application from PCT (US) application GB 99/02256 (Publication N° WO 00/02544) filed 13 Jul. 1990.

FIELD OF THE INVENTION

This invention relates to the treatment of skin conditions, comprising those conditions requiring stimulation of melanocyte proliferation and to the inhibition of melanomas. The invention is of especial application to the treatment of vitiligo and skin cancer.

Vitiligo is a common skin pigment disorder characterised by the development of patchy de-pigmented lesions. Current treatments which include the use of photosensitisers (eg psoralens) with UVA radiation (PUVA), corticosteroids or skin grafting have low success rates and are generally accompanied by unpleasant side effects. Vitiligo has a highly detrimental impact on the emotional well-being of the sufferer, the disfiguring effects of the disease being compounded by the absence of a suitable treatment. Although vitiligo patches are not believed to contain melanocytes (pigment producing cells), a reservoir exists in hair follicles in vitiliginous skin. Thus activation of hair follicular melanocytes is a crucial process in the repigmentation of vitiliginous skin.

Certain plant remedies, usually administered as mixtures of herbs or extracts, particularly those used in traditional Chinese medicine and Indian Ayurvedic medicine, have been employed for the treatment of vitiligo for a long time and in many cases have given positive results in small scale studies. Herbs such as *Psoralea corylifolia* L. and *Vernonia anthelmintica* Willd. (=*Centratherum anthelminticum Kuntze*) are well known for their use in this disease. Psoralens, which are employed in the modern PUVA and khellin in KUVA therapy were originally derived from plant sources (*Psoralea corylifolia* L. and *Ammi visnaga* respectively) used in traditional remedies for vitiligo. However these therapies rely on the use of UV irradiation for their efficacy, which is associated with the aetiology of skin cancer.

The fruit of black pepper (*Piper nigrum* L.) and long pepper (*Piper longum* L.) are both important medicinal herbs in Ayurvedic and Unani (traditional Indian) medicine systems, in which remedies generally consist of mixtures of herbs. A wide range of the medicinal uses of black pepper have been documented by Kirtikar and Basu (Indiam Medicinal Plants, $2^{nd}$ Edition, Vol. 3, (1935) pages 2128–2135), including its use in the treatment of leucoderma. Black pepper has also been implicated as a possible adjunct to *Vernonia anthelmintica* in the treatment of leucoderma (Indian Medicinal Journal, Vol. 1, $3^{rd}$ Edition, (1982) 1267–1270). These two herbs are employed as a constituent in many traditional herbal preparations for a variety of uses, including gastro-intestinal and skin ailments. Compositions comprising black pepper, ginger and pipali have been used in the treatment of vitiligo (Ancient Science of Life, Vol. IX, No. 4 (1990) 202–206); however, the specific therapeutic action of black pepper in this orally administered composition has not been established.

There is, therefore, a need for further compounds and compositions, which are able to stimulate the proliferation of melanocytes.

SUMMARY OF THE INVENTION

It has been surprisingly found that, piperine, which is present in the fruit of *Piper nigrum*, stimulates the replication of melanocytes. The action of piperine is to increase the number of cells which confer pigmentation. Piperine is the compound (E,E)-1-[5-(1,3-benzodioxol-5-yl)-1-oxo-2,4-pentadienyl]piperidine and should not be confused with piperidine.

Piperine has also been reported to occur in other Piper species ie. *P. acutisleginum, album, argyrophylum, attenuatum, aurantiacum, betle, callosum, chaba, cubeba, guineense, hancei, khasiana, longum, macropodum, nepalense, novae hollandiae, peepuloides, retrofractum, sylvaticum*. Pharmaceutical compositions containing piperine have been used in the treatment of tuberculosis and leprosy (EP 0 650 728). It has also been suggested that piperine is able to enhance the bioavailability of the other constituents of a pharmaceutical composition (WO 96/25939).

The invention provides a method of treating a subject (human or animal) having a skin condition requiring stimulation of melanocyte proliferation and melanomas, which comprises administering to the subject, preferably to the site of the condition, an effective amount of piperine or an active analogue or derivative thereof, as hereinafter defined.

The active ingredient may be used on its own, but is more suitably used in combination with a carrier or excipient and optionally one or more further active ingredients. It may also be used in the form of an isolate or plant extract, in the case of piperine itself derivable from *Piper nigrum*, for example.

Stimulation of melanocyte proliferation greatly facilitates the re-pigmentation of de-pigmented skin, e.g. post traumatised de-pigmented skin. The term "post traumatised de-pigmented skin" means the skin formed during the healing process that occurs after a skin trauma. De-pigmentation may arise, for example, from scar tissue formed as a result of a skin trauma such as burn or other skin lesion or may be due to vitiligo. The present invention can be used to treat any of these skin disorders in a patient.

Generally in this invention, the piperine or active derivative or analogue thereof may be administered by oral, topical, intravenous or subcutaneous (intramuscular) routes but is preferably applied topically (to the area of the skin where treatment is desired).

The active ingredient may be formulated as a solid powder; a paste, ointment or cream; a tablet or capsules; or a solution.

The method of the invention may also be used to treat a person having a skin condition which would benefit from coloration, e.g. to enhance or promote the natural colouring of the skin. The treatment may be used for prophylactic, therapeutic or cosmetic purposes.

Piperine and its analogues or derivatives as hereinafter defined inhibit the proliferation of melanoma cells. Thus, they may also be used in the treatment of skin cancer. Another aspect of the invention therefore provides a method of treating skin cancer in a human or animal patient comprising the administration to said patient of a therapeutically effective amount of piperine or an active analogue or derivative thereof, as hereinafter defined.

The piperine or active analogue or derivative thereof may be administered by oral or topical routes. Suitable dosage forms may be any of those discussed above.

The formula of piperine and derivatives and analogues thereof usable in this invention is given below.

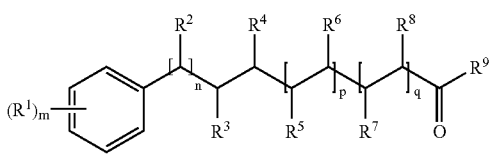

(1)

wherein n=0 or 1;
p is 0 or 1;
q is 0 or 1
when n=p=q=0, $R^3$ and $R^4$ represent hydrogen or together represent a carbon to carbon double bond;
when n=0 and one of p and q=1, $R^3$ and $R^4$ together and one of $R^5$ and $R^6$ together or $R^7$ and $R^8$ together represent carbon to carbon double bonds, $R^3$ and $R^4$ together represent a carbon to carbon double bond and $R^5$ and $R^6$ or $R^7$ and $R^8$ represent hydrogen atoms, $R^3$ and $R^4$ represent hydrogen and one of $R^5$ and $R^6$ together or $R^7$ and $R^8$ together represent carbon to carbon double bonds or $R^3, R^4, R^5, R^6, R^7$ and $R^8$ all represent hydrogen atoms;
when n=0 and p=q=1, $R^3$ and $R^4$ together and one of $R^5$ and $R^6$ together or $R^7$ and $R^8$ together represent carbon to carbon double bonds the other of $R^5, R^6, R^7$ and $R^8$ representing hydrogen, $R^3$ and $R^4$ together represent a carbon to carbon double bond and $R^5$ and $R^6$ or $R^7$ and $R^8$ represent hydrogen atoms, $R^3$ and $R^4$ represent hydrogen and one of $R^5$ and $R^6$ together or $R^7$ and $R^8$ together represent carbon to carbon double bonds the other of $R^5, R^6, R^7$ and $R^8$ representing hydrogen, $R^3$ and $R^4$ together, $R^5$ and $R^6$ together and $R^7$ and $R^8$ together represent carbon to carbon double bonds or $R^3, R^4, R^5, R^6, R^7$ and $R^8$ all represent hydrogen atoms;
or optionally when n is 1 $R^2$ and $R^3$ together represent a carbon to carbon double bond and one or more of $R^4$ and $R^5$ together, $R^5$ and $R^6$ together, $R^6$ and $R^7$ together or $R^7$ and $R^8$ together represent a carbon to carbon double bond the other of $R^4$ to $R^8$ representing hydrogen;
m=1, 2 or 3;
when m=1, $R^1$ represents an alkoxy group having from 1 to 3 carbon atoms or a hydroxy group;
when m=2, each $R^1$ independently represents an alkoxy group having from 1 to 3 carbon atoms or the two $R^1$s together represent a 3',4'-methylenedioxy group;
when m=3, two $R^1$s together represent a 3',4'-methylenedioxy group and the other $R^1$ represents an alkoxy group having from 1 to 3 carbon atoms or a hydroxy group;
$R^9$ represents a pyrrolidino, piperidino, 4-methylpiperidino or morpholino group, a N-monoalkylamino group of 4 to 6 carbon atoms, a N-monocycloalkylamino group of 4 to 7 carbon atoms, a 3',4'-methylenedioxy-substituted benzylamino or 2-phenethylamino group or $R^9$ represents an alkoxy group of 1 to 6 carbon atoms; in any of its E, Z geometrically isomeric forms.

Certain of the active analogues or derivatives of piperine of formula (1) are new. The present invention therefore includes such compounds, and pharmaceutical compositions containing them together with a carrier or excipient.

DESCRIPTION OF THE PREFERRED EMBODIMENTS

Figure 1:
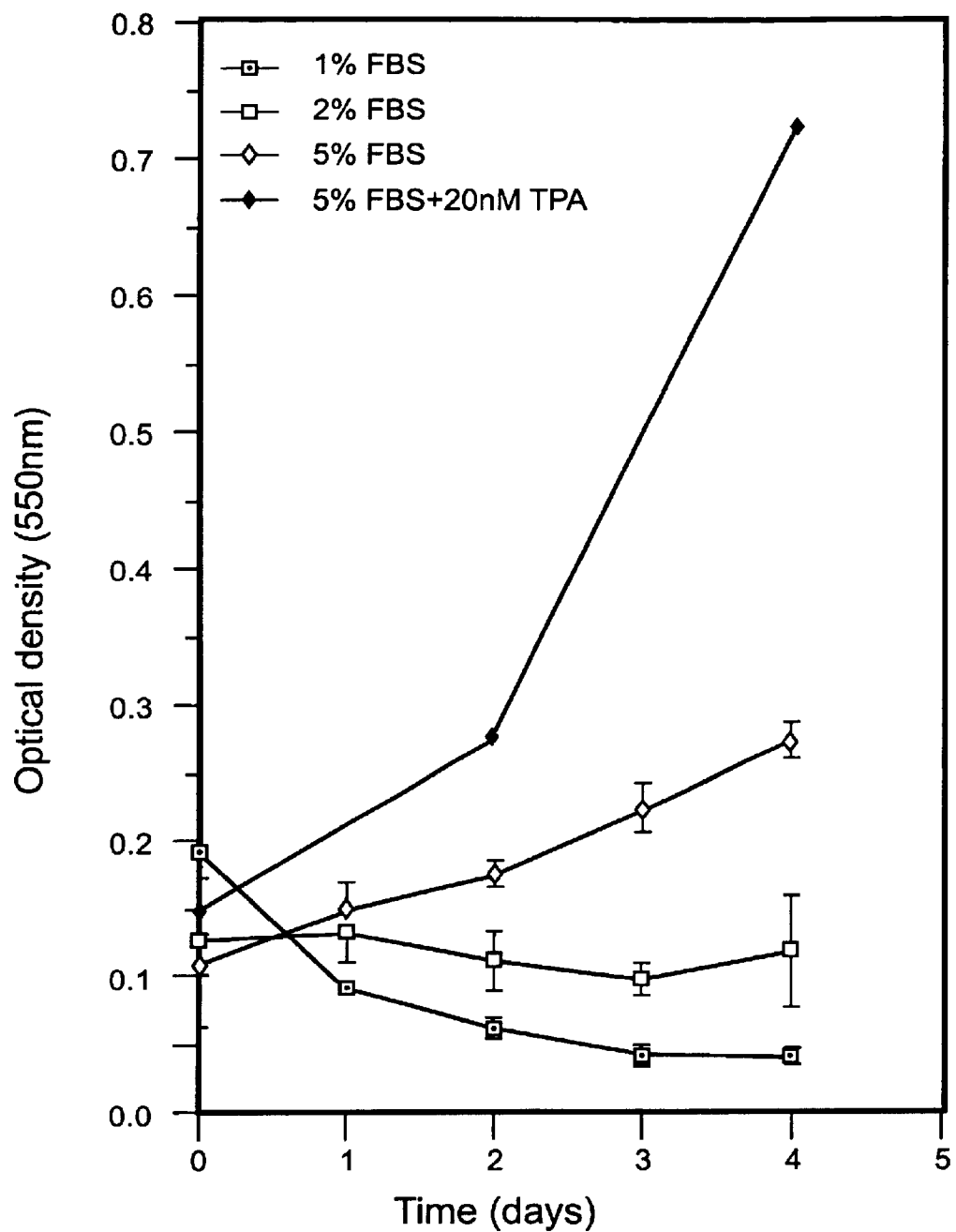
FIG. 1: Plots of growth of melan-a-cells cultured in different media. Each point represents the mean and standard deviation (SD) of 6 replicates. FBS=fetal bovine serum. TPA=tetradecanoyl phorbol acetate.

One useful class of compounds of formula (1) is that in which
(a) n is 0, p and q are each 0 or 1, m is 2, the $R^1$s together represent a 3',4'-methylenedioxy group, $R^3$ and $R^4$, together with the carbon atoms to which they are attached form a carbon to carbon double bond and, when p and q are each 0 or 1, $R^5$ and $R^6$ and $R^7$ and $R^8$ together with the carbon atoms to which they are attached, form a carbon to carbon double bond and $R^9$ is piperidino, or
(b) n is 0, one of p or q is 1 and (i) m is 3, the $R^1$s being 3',4'-methylenedioxy and 6'-methoxy or (ii) m is 2, the $R^1$s being 3'-hydroxy-4'-methoxy; or (iii) m is 1 and the $R^1$ is 4'-hydroxy; and $R^3$ to $R^9$ are as defined in case (a) above, or
(c) n is 0, one of p and q is 1, $R^9$ is piperidino, pyrrolidino, isobutylamino or methoxy and all other symbols are as defined in case (a) above, or
(d) n is 0, one of p and q is 1, $R^5, R^6, R^7$ and $R^8$ represent hydrogen atoms and either $R^3$ and $R^4$ also do or $R^3$ and $R^4$ together with the carbon atoms to which they are attached form a carbon to carbon double bond; and m, $R^1$ and $R^9$ are as defined in case (a) above;
(e) n is 0, p=q=1 and $R^3, R^4, R^5, R^6, R^7$ and $R^8$ represent hydrogen;
(f) n is 0, one of p and q is 1, $R^3, R^4, R^5, R^6, R^7$ and RS represent hydrogen and $R^9$ is cyclohexylamino; and
in all of which cases (a) to (f) the molecule is in the E,E or all E geometric configuration or in case (a) when n is 1 may be in the Z,Z, Z,E or E,Z geometric configuration.

The following are preferred features of the compounds of formula (1) considered alone or in any possible combination of two or more:
n is 0, one of p and q is 1, $R^3$ and $R^4$ together and one of $R^5$ and $R^6$ together or $R^7$ and $R^8$ together represent double bonds or $R^3$, $R^4$, $R^5$, $R^6$, $R^7$ and $R^8$ all represent hydrogen atoms m is 2 or 3, two $R^1$s represent 3',4'-methylenedioxy and optionally a third $R^1$, representing 6'-methoxy, is also present $R^9$ represents a piperidino, 4-methylpiperidino, pyrrolidino or morpholino group or an alkylamino group having 4 to 6 atoms, preferably branched chain and especially an isobutylamino (2-methylpropylamino) group, a cycloalkyl amino group of 4 to 7 carbon atoms, especially a cyclohexylamino group, or a 3,4-methylenedioxy-substituted benzylamino or 2-phenethylamino group alternatively $R^9$ is an alkoxy group having from 1 to 6 carbon atoms, preferably 3 to 6 the geometric configuration at the double bonds is as in piperine (all E, E)

While the preferred meaning of $R^1$ is a 3',4'-methylenedioxy group, $R^1$ may alternatively be provided by one, two or even three groups selected from hydroxy and alkoxy of 1 to 3 carbon atoms, preferably methoxy, e.g. as in 3'-methoxy, 4'-methoxy, 6'-methoxy and 3',4'-dimethoxy substitution of the left-hand benzene ring.

The twice-daily topical application of compounds of formula (1) has been found to induce significant pigmentation in mice. Skin coloration in the mouse population under study was first observed at approximately four weeks after the treatment was started. This coloration was enhanced further as a result of subsequent topical applications.

Specific preferred compounds for use in the invention are as follows:

Variations and alterations (all other structural features of the molecule are as in piperine unless otherwise indicated)

| | Compounds of formula (1) and trivial names |
|---|---|
| Variation in stereochemistry at double bonds and in extent of conjugation in chain 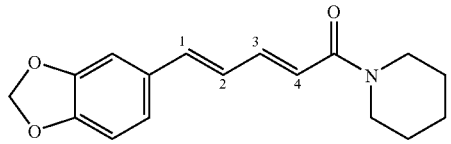 | 1 (E, E) - Piperine<br>2 (Z, Z) - Chavicine<br>3 (Z, E) - Isopiperine<br>4 (E, Z) - Isochavicine<br>5 3,4-dihydropiperine - Piperanine<br>6 1,2,3,4-tetrahydropiperine |
| Variation in separation of rings (conjugated) 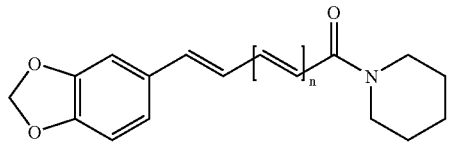 | Structures (all E)<br>7 n = 0 - Ilepcimide<br>1 n = 1 - Piperine<br>8 n = 2 - Piperettine |
| Alterations to nitrogen substituent 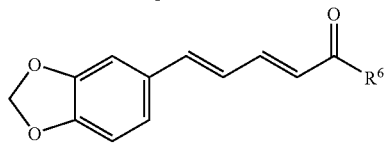 | Structures (all E, E)<br>$R^6$ =<br>1 piperidino - Piperine<br>9 pyrrolidino - Trichostachine<br>10 isobutylamino - Piperlonguminine<br>11 methoxy - Despiperidylmethoxypiperine<br>17 morpholino<br>18 hexylamino<br>19 3',4'-methylenedioxybenzylamino |
| Alterations to the phenyl substituent 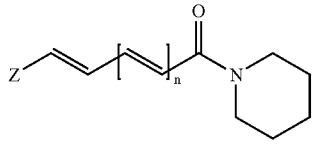 | Structures (all E, E)<br>Z = <br>1 3',4'-methylenedioxyphenyl; n = 1 - Piperine<br>12 As 1 +6'-methoxy; n = 1; - Wisanine<br>13 3'-hydroxy, 4'-methoxyphenyl; n = 1 - 4'-Methoxyisocoumaperine<br>14 4'-hydroxyphenyl; n = 1 - Coumaperine<br>20 4'-methoxyphenyl; n = 0 |
| Alterations to connecting chain and amide group 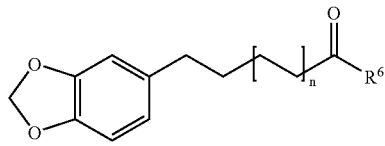 | 21 cyclohexylamino; n = 1<br>22 cyclohexylamino; n = 0 |

The naturally occurring compounds (including piperine) can be extracted from suitable plant sources or synthesised using methods known to a skilled person (see, for example, Chapman and Hall, Combined Chemical Dictionary on CD-Rom, Release 1:1 (1997) and The Merck Index (1983), 10th edition. Publ. Merck and Co, Rahway, USA. PP. 1077–1078 (except compounds 2 and 3)). Many of the above, occur in *P. nigrum* or other *Piper* species (10 and 12).

Compounds 2 and 3 can be prepared by isolation from *P. nigrum* using methods known to a skilled person (see, for example, Cleyn R De and Verzele M (1975). Constituents of-Peppers. Part VII. Spectroscopic Structure Elucidation of Piperine and its Isomers. Bulletin de la Societe Chimique Belgique, 84, 435–438).

Compound 6 can be prepared by hydrogenation of piperine, using known methods.

Compound 11 can be prepared by methanolysis of piperine using sodium methoxide.

Compound 13 can be prepared from 3-hydroxy-4-methoxybenzaldehyde using methods analogous to those used for the preparation of piperine.

Other compounds within formula (1) can be prepared from the appropriate acid with the appropriate connecting chain between the carboxylic acid function and the benzene ring and having the appropriate stereochemistry. Where necessary, this may be preceded or followed by reduction to reduce the double bond or bonds in the connecting chain. Methods of preparing amides and esters from these acids are illustrated by the Examples below. They may also be adapted from the references cited herein, the disclosure of which is herein incorporated by reference.

The active compounds may be formulated for topical use in the form of creams, soft paraffin or lotions. Aqueous cream BP or Yellow Soft Paraffin BP may suitably contain the active at 0.03–3.0 mg % w/w or an equivalent amount of plant extract. A suitable lotion is typically prepared from 20% glycerol and 80% ethanol in purified water and contains 0.03–3.0 mg % w/w of the active material. These topical formulations may also contain penetration enhancers such as oleic acid, propylene glycol, ethanol, urea, lauric diethanolamide or azone, dimethyl sulphoxide, decylmethyl sulphoxide, or pyrrolidone derivatives. Liposomal delivery systems may also be used.

Compositions for oral formulation include tablets or capsules containing 1.5–150 mg active or equivalent amount of plant extract.

The invention will now be described with reference to the following non-limiting examples, with reference to the accompanying tables and drawings.

EXAMPLES

Plant Samples and Preparation of Extracts

*Piper nigrum* L. fruit (black pepper, Piperaceae), originally from India, was purchased from the Food Centre, 70 Turnpike Lane, London N8, UK. The rest of the herbs were either supplied by East-West Herbs, Kingham, Oxon, UK or by Cipla Ltd, Mumbai, India.

For the preliminary screening programme, the powdered dry herb (10 g) was heated to boiling in distilled water (100 ml) and allowed to boil for 10 min, using a hot plate as heat source. The plant material was filtered off under vacuum through filter paper (Whatman), and the filtrate freeze-dried.

Cell Culture Experiments

Microplate Culture and Sulforhodamine B (SRB) Assay

Cells of mouse melan-a cell line (passage number 18–24), a first known line of non-tumorigenic pigmented mouse melanocytes were maintained in a flask (Costar, Cambridge, Mass., USA) using RPMI 1640 (ICN, Costa, Mesa, Calif., USA) as a basic medium. For microplate proliferation assays, subconfluent melan-a cultures were trypsinized (0.25% trypsin at 37° C. for 5–10 min) and inoculated with a repeater-pipettor (Finn pipette, Labsystems, Finland) into 96-well microtiter plates (Costar, Cambridge, Mass., USA). The plates were incubated at 37° C. in a 10% $CO_2$, 90% air humidified atmosphere for the stated length of time. At the end of the incubation, an SRB assay was performed. Briefly, cells attached to the bottom of the plate were fixed by addition of cold trichloroacetic acid (TCA, 4° C., Aldrich, Dorset, UK) on the top of the growth medium (final TCA 20% w/v). The plate was placed at 4° C. for 1 hour before being gently washed five times with tap water. It was allowed to dry in air, or aided with a hair dryer to speed up the drying process, then 50 μl of 4% w/v SRB dissolved in 1% acetic acid in water was added to each well for 30 min. At the end of the staining period, unbound SRB was removed by washing 4 times with 1% acetic acid. The plate was air dried again, and 150 μl of 10 mM aqueous Tris base (Sigma-Aldrich Co. Ltd, Irvine, UK) was added into each well to solubilize the cell-bound dye. The plate was shaken for 15 min on a gyratory shaker followed by reading the optical density (OD) at 550 nm in a microplate spectrophotometer (Anthos Labtec HT3, version 1.06)

Example 1

Optimisation of Incubation Conditions—FBS Concentration and Cell Seeding Density Prior to testing the herbal extracts, optimal culture conditions were established. The variable factors regarding incubation conditions include foetal bovine serum (FBS) concentration, initial cell seeding density and incubation period. To determine optimum FBS concentration, 1, 2, and 5% FBS were used to culture the melan-a cell line, the growth pattern with each concentration of FBS was monitored by SRB assay. For the determination of optimum cell seeding density, a series of initial seeding density of 0.15 to $1.2 \times 10^4$ cell per well of melan-a cells were plated into 96-well plates with 5% FBS and 20 nM tetradecanoyl phorbol acetate (TPA) supplemented growth medium. The growth pattern was monitored with SRB assay at daily intervals. The culture was extended to 8 days; on day 4, the medium in the remaining plates was replaced.

Results

The Effect of FBS Concentrations on Melan-a Growth

The optimal condition for the negative experimental control, is that cells neither grow too fast nor decline dramatically. Rapid growth might mask any subtle stimulatory effect brought about by the herbal extracts, whereas a dramatic decline in cell numbers indicates unfavourable culture conditions for cell survival, which could lead to cell damage. FIG. 1 shows the growth curves of melan-a cell line at three different concentrations of FBS. Neither 1% nor 2% FBS supplemented medium was able to maintain cell survival; cell numbers declined significantly in 4 days of culture. However, 5% FBS was capable of keeping melan-a cell line alive with only a small increase in cell numbers observed over 4 days. TPA (20 nM) was able to cause further proliferation in the presence of 5% FBS indicating that cells were capable of responding to mitogenic stimuli at 5% FBS. Morphological observations under a microscope revealed that with 1% and 2% FBS supplemented medium, cell bodies were round, lightly pigmented with few dendritic processes and the culture displayed an ageing growth pattern. However in 5% FBS, cells possessed more melanosomes and some short dendrites without an ageing appearance. Therefore 5% FBS was used throughout in the herbal screening experiments.

Growth Curves of Melan-a Cell Line with Various Seeding Densities

Figure 2:
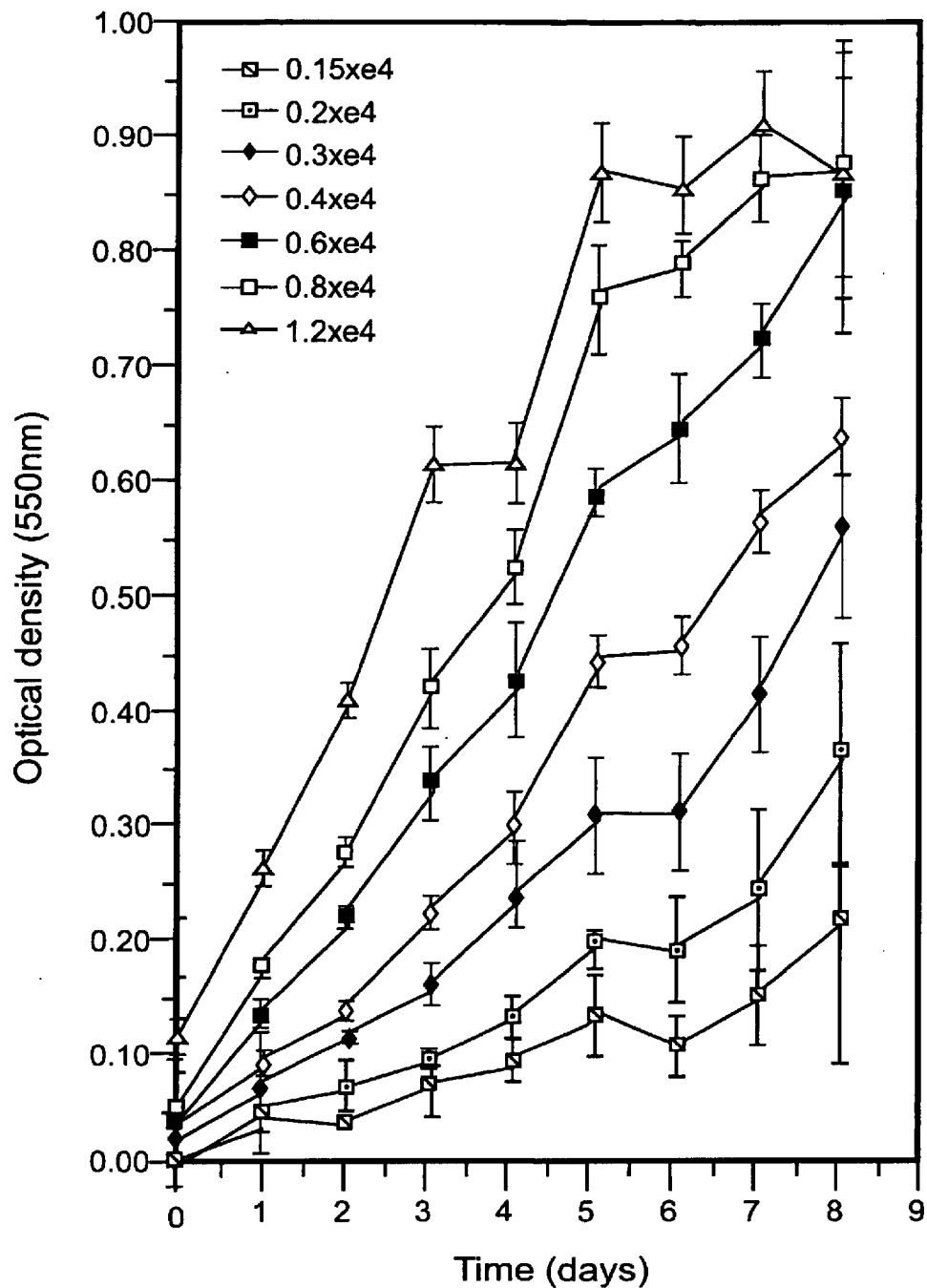
FIG. 2: Plots of growth melan-a-cells cultured from different initial plating densities of cells. Medium was supplemented with 20 nM TPA. On day 4 the medium in the remaining plates was replaced. Each point shows mean and SD of 6 replicates.

In FIG. 2, growth curves over 8 days with different initial cell numbers were plotted to elucidate the melan-a cell line's growth pattern in 96-well plates in the presence of 5% FBS and 20 nM TPA. The optimal initial plating density together with proper harvesting time was determined. All of the initial plating number of cells showed a net growth in the presence of TPA and 5% FBS supplemented medium, although the higher plating density of $1.2 \times 10^4$ cells/well depleted the growth medium on day 3 of culture and the cells ceased to grow until the medium was replaced. With the lower plating densities ($2-4 \times 10^3$ cells/well) the SRB assay OD readings remained relatively low after 8 days' culture. The initial plating density of $6 \times 10^3$ cells/well exhibited exponential growth, and after 4 days of culture, the OD reading increased to a value of about 0.4. Since the higher OD values are associated with greater precision and accuracy, it was determined that the initial inoculation of $6 \times 10^3$ cells/well was the optimum density for the herbal test experiment. For the simplicity of the experiment, harvesting time was day 4 since the cells at this stage was not confluent and after 4 days, growth medium tended to become depleted and replacement was necessary for the further growth.

Example 2
Preliminary Herbal Screening Experiments

Melan-a cells were seeded at a density of $6 \times 10^3 / 100$ μl/well in standard medium supplemented with 0 nM TPA and 5% FBS. After 4 hours of incubation, herbal extracts, which were reconstituted in growth medium and sterilised by filtration (pore size 0.2 μm), of different concentrations was added into each well. Final concentrations of plant extract were 0 (negative control), 10, 100 and 1000 μg dry extract per ml. 6 replicate wells were used for each concentration tested. The negative control (12 wells), positive control (20 nM TPA, 6 wells), and test wells were all in the same 96-well plate. The culture was terminated after 4 days and SRB assay performed according to the methods given above.

Results
The Effect of 30 Herbal Extracts on the Proliferation of Melan-a Cell Line Table 1 shows the results of the preliminary screening of 30 aqueous herbal extracts on the proliferation of melan-a cell line. Crude extracts of *Astragalits membranaceous* (Fisch.) Bunge, unripe *Citrus reticulata* Blanco, *Dictamnus dasycarpus* Turcz., *Ophiopogon japonicus* (Thunb.) Kergawe, *Piper nigrum* L., *Poria cocos* (Schw.) Wolf and *Tribulus terestris* L. were observed to stimulate melanocyte proliferation, sometimes even at the lowest dose level of 10 μg/ml. Other extracts either had no significant effect or were cytotoxic. Among these positive responses, that of *Piper nigrum* L. extract at 0.01 and 0.1 mg/ml was the most pronounced. *Piper nigrum* extract at these two concentrations not only strikingly enhanced cell growth, but this extract also altered the cell morphology. In the presence of *Piper nigrum* extract, the cellular bodies were smaller, with more and longer bipolar or polydendritic processes, an effect similar to that observed with TPA.

Example 3
Repeats of the Tests on *Piper nigrum* Extract on the Melan-a Cells A newly prepared *Piper nigrum* fruit extract was tested on a new batch of melan-a cell line with the culture in microplates extended to 8 days. The effects of *Piper nigrum* extract on the growth of melan-a cell line were evaluated by SRB assay.

Results
Repeats of the Tests of *Piper nigrum* Extract on Melan-a Cells

Figure 3:
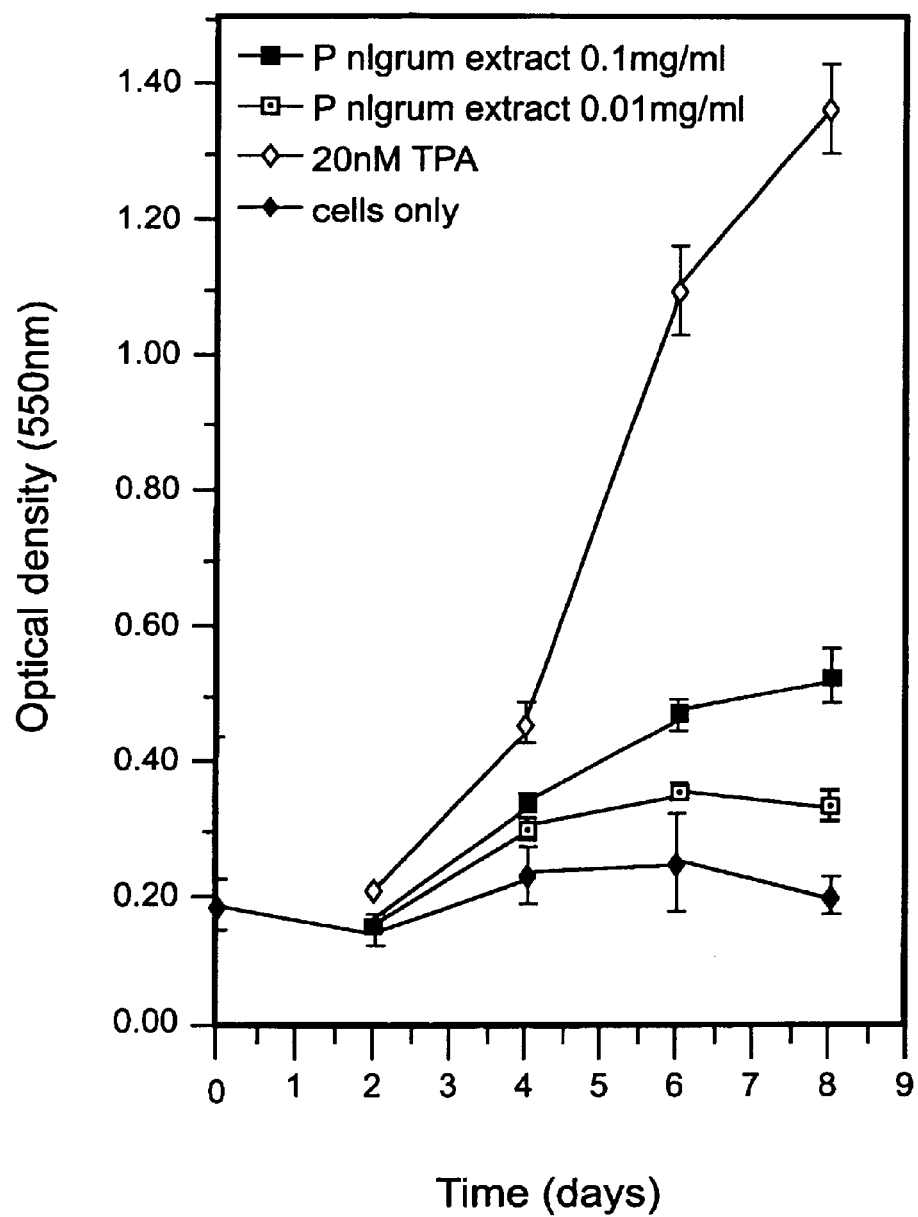
FIG. 3: Effect of P. nigrum extract on the growth of melan-a cells. Culture was maintained for 8 days. Medium and extract were replaced with fresh ones on day 4. Each point designates mean and SD of 6 replicates, except that 12 replicates were done for cells only.

In the light of the positive results from the preliminary experiment, further investigations on *Piper nigrum* extract were carried out. FIG. 3 shows that the result of the significant proliferant effect brought about by the *Piper nigrum* extract was even more marked on the extension of the incubation period to 8 days of culture, the growth was 272% of the control (cells only). Microscopically, the morphology of the cells was altered as those seen in the preliminary experiments.

Example 4
Confirmation of the Proliferant Effect of *Piper nigrum* by Haemocytometer Counting Melan-a cells were plated in petri dishes (Ø35 mm, Nunclon, Denmark) with a plating density of $2 \times 10^4$/ml and *Piper nigrum* extract at concentrations of 0.01 and 0.1 mg/ml. A negative control (cells in medium only) and positive TPA (20 nM) control were also set up. After 4 days the cells in each dish were harvested and counted with haemocytometer.

Results
Confirmation of the Proliferant Effect of *Piper nigrum* by Haemocytometer Counting SRB assay indirectly estimates cell number through protein staining and spectrophotometric measurement. To confirm if *Piper nignim* extract stimulates melan-a cell proliferation, a direct cell counting with haemocytometer method was employed. Table 2 shows the cell numbers in the presence of *Piper nigrum* extract and 20 nM TPA. Cell number under the influence of *Piper nigrum* extract at 0.01 and 0.1 mg/ml were increased significantly compared to control, but less than that with 20 nM TPA. This result is consistent with the finding in 96-well microplate SRB assay.

Example 5
Effect of Piperine on the Growth of Melan-a Cell Line

Piperine (Sigma-Aldrich Co. Ltd, Irvine, UK) was dissolved in MeOH, sterilised by filtration through a membrane (pore size 0.2 μm) and diluted with standard growth medium. The final concentrations in culture were 0.1 and 1 μM. A separate experiment (data not shown) showed that the concentration of MeOH present in these experiments was not toxic or proliferant to the cells.

Results
The Effect of Piperine on the Proliferation of Melan-a Cell Line

Figure 4:
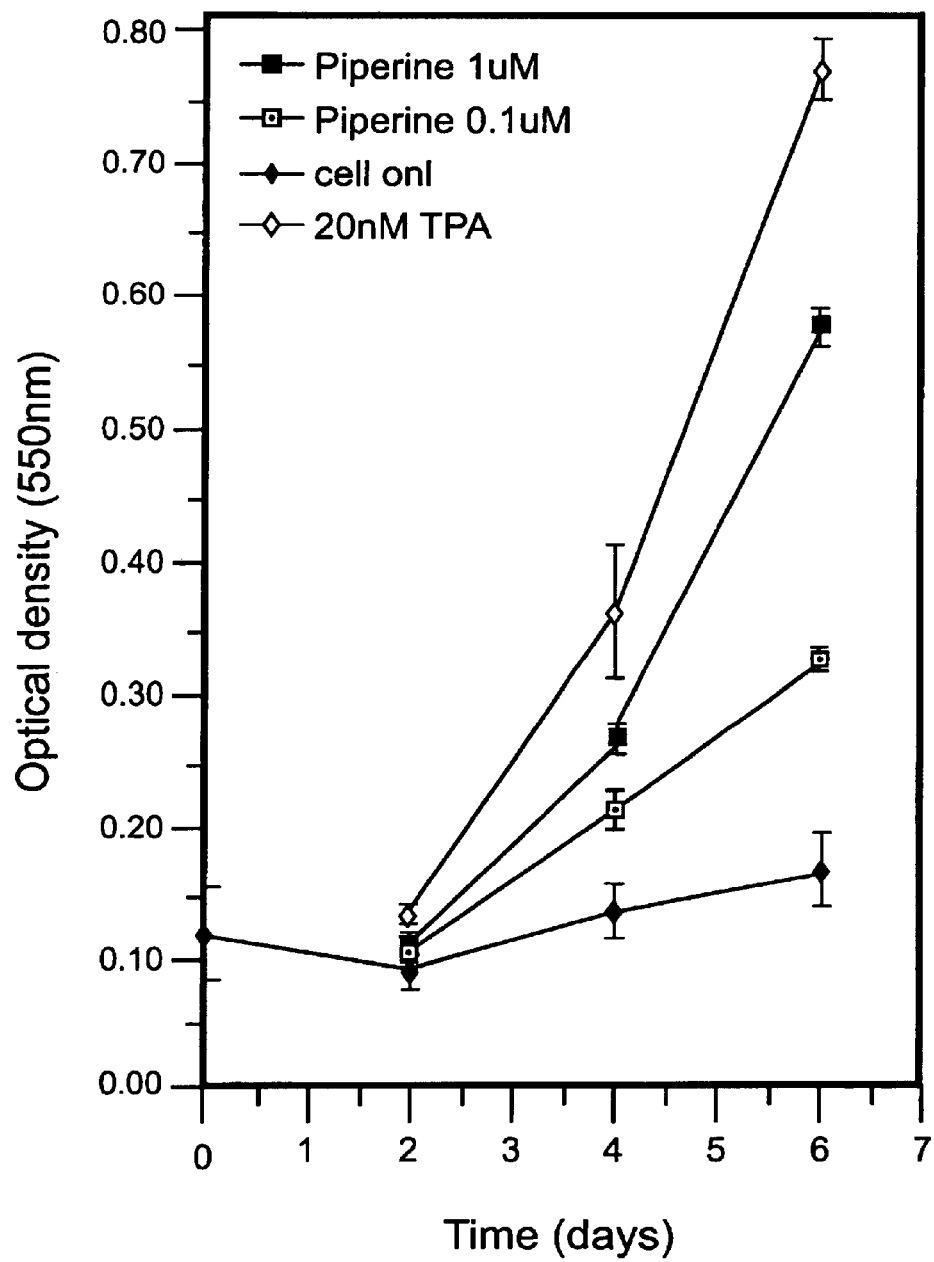
FIG. 4: Effects of P. nigrum extract and TPA on the proliferation of melan-a cell line. Each point shows mean and SD of 6 replicates, except that 12 replicates were done for cells only.

The effect of this compound on melan-a cell line is shown in FIG. 4. Piperine at the two concentrations tested significantly stimulated melan-a proliferation. This compound brought about morphologic changes to melan-a cells, with smaller cell bodies, more and longer cellular dendrites, resembling those alterations induced by *Piper nigrum* extract and TPA. This indicates that piperine is an active principle responsible for the observed proliferant effect of *Piper nigrum*.

Example 6
Test of Piperine on Different Cell Types to Determine its Specificity In order to determine the specificity of piperine, a panel of different cell types were employed to facilitate this investigation. These included melan-a, melan-c, SVK14, CSM, XB2, SC1, B16F10, IM9, CACO2, Swiss 3T3 cell lines and normal human lymphocytes. TPA (20 nM) was also tested on these cells. Table 3 shows the biological origin of the cells and an outline of the cell culture protocols.

Results
The Effects of Piperine and TPA on the Growth of a Panel of Cell Types.

From Table 4, it can be seen that piperine has a highly selective effect on the growth of a panel of cell types, since it only stimulates the mouse melanocytes (melan-a, melan-c), human melanoblasts (FM21E), human foetal melanocytes (FM 21E) and the mouse fibroblast SC1 cell lines at the concentration tested. The SC1 cell line may have a particular sensitivity to TPA due to the way in which it has been derived, i.e. it has been cultured in the presence of TPA. However, piperine has either no effect or a cytotoxic effect on other cells. This result implies that piperine may have desirable specificity index for the proliferation of melanocytes in culture and is not a general mitogen. In our experimental system, TPA, a well known PKC activator and a tumour promoting agent, had similar effects to piperine on all cell types tested, except that TPA strikingly stimulated human lymphocyte and 3T3 fibroblast proliferation whereas piperine obviously lacked such an activity. Piperine seems to be a less potent stimulant than TPA.

Example 7
Mode of Action: Effect of RO-31-8220 on the Growth of Melan-a Cells with Piperine and TPA Melan-a cell line cultured with piperine 1 µM and TPA 20 nM separately was set up in a 96-well plate, 1 µl of different concentrations of RO-31-8220 (Calbiochem-Novabiochem) in DMSO was introduced with a micro-syringe into the wells to make up the final RO-31-8220 concentrations of 0 (control), 0.1, 1, 5, 10, 100 nM, with final DMSO concentrations smaller than 0.01% v/v, at which the DMSO showed neither toxic nor proliferant effect to the cells in a separate experiment (data not shown). 6 replicate wells were used for each concentration. The culture was incubated for 4 days before it was terminated and processed with SRB assay to evaluate the growth of melan-a cells.

Figure 5:
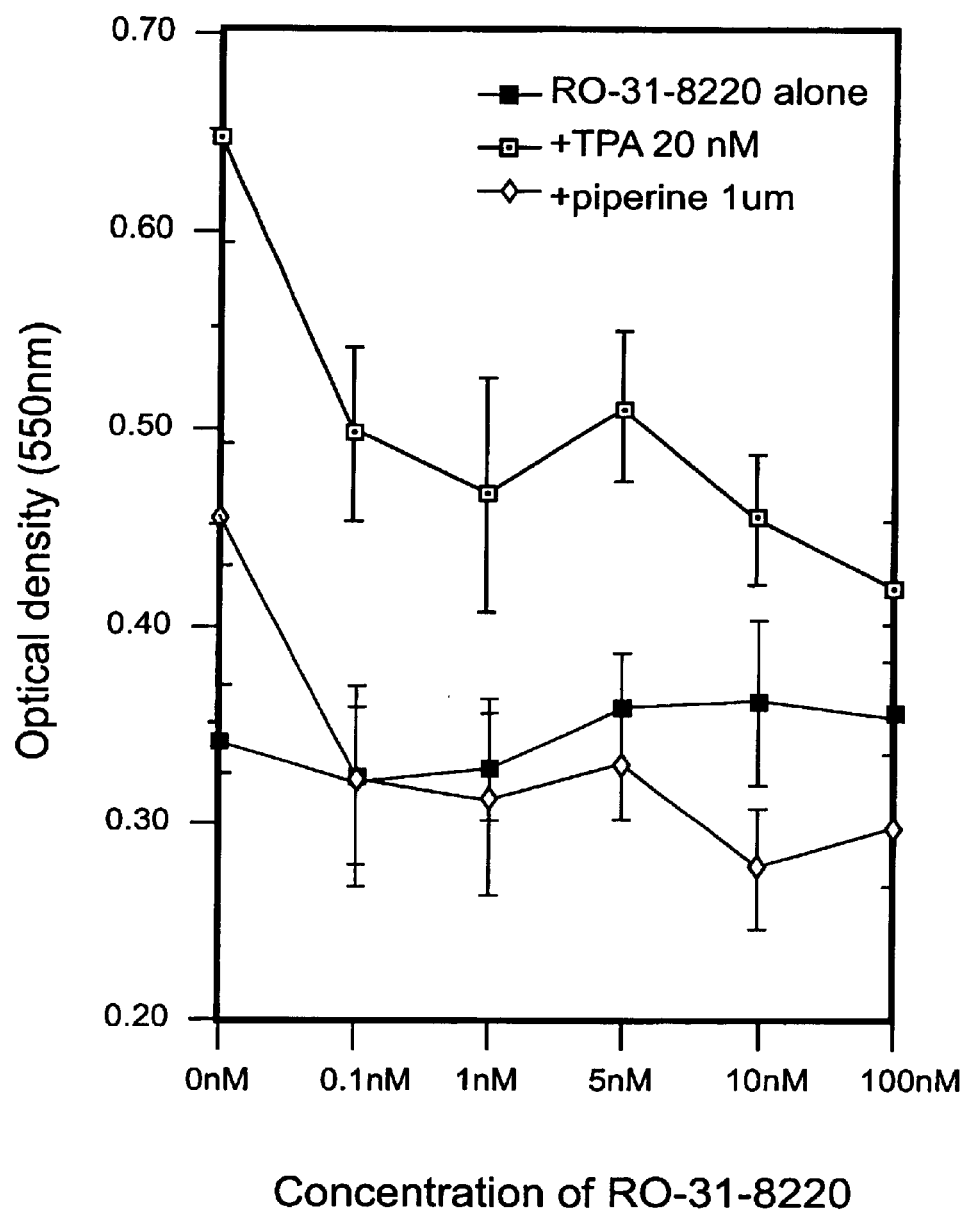
FIG. 5: Effects of piperine and TPA on the growth of melan-a cells in the presence of RO-31-8220. n=6 for piperine and TPA treated wells, whereas n=12 for RO-31-8220 alone.

Results
Mode of Action: Effect of RO-31-8220 on the Growth of Melan-a Cells with Piperine and TPA FIG. 5 shows the effect of RO-31-8220 on the survival and growth of melan-a cell line in the presence or absence of piperine and TPA. RO-31-8220 alone did not have significant cytotoxic effect to the cells at the concentrations up to 100 nM. However, the proliferant effects of piperine, and TPA (as indicated by the Y axis values) on melan-a cells were effectively inhibited by the presence of RO-31-8220 at the concentrations of 0.1–100 nM. It thus appears that piperine and TPA exert their proliferant effects through the activation of PKC cell signalling pathway.

The selectivity of piperine on the growth of a panel of cell types has also been tested. It was found that piperine possessed a fairly high specificity and selectivity towards melanocytes, since it significantly stimulated the growth of melan-a, melan-c and FM21E melanoblasts and FM21E melanocytes in culture, whereas it did not stimulate all other cells apart from a TPA-sensitive fibroblast cell line. Piperine was observed to have inhibitory effects on B16 mouse melanoma cell line which is syngeneic with melan-a cells. Thus piperine may be a specific stimulant for the proliferation of melanocytes in vitiliginous skin without the risk of stimulating melanoma cells.

Example 8
Experiments on Human Melanoblasts in Culture

Human melanoblasts in culture in this experiment were established from human foetal skin. Subconfluent melanoblasts maintained in MCDB 153 medium supplemented with 10% FBS, 10 ng/ml stem cell factor (SCF) and 1 mM endothelin 3 were subcultured and inoculated into 96-well microplate with $6 \times 10^3$ cells/100 µl/well. After incubation in the 10% $CO_2$, humidified atmosphere, at 37° C. for 3–4 hours to allow the attachment of the cells on the plate, piperine dissolved in MeOH and water was added into the wells. The final concentrations of piperine were 1, 5, 10, 100 µM, with TPA (20 nM) as positive control. Six replicates were used in each group of treatment, with 12 wells used for vehicle control. The incubation was conducted for 5 days before cells were harvested by fixing with cold trichloroacetic acid (TCA, at 4° C., final concentration 20% v/v), and evaluated for cell number using an SRB assay. One way ANOVA and Dunnett's t-test was employed to test the significance of any differences between treatment groups and vehicle control. Growth in the presence of piperine and TPA was expressed as % of control incubations containing no piperine or TPA. The experiments were repeated using melanoblasts from 3 different donors.

Figure 6:
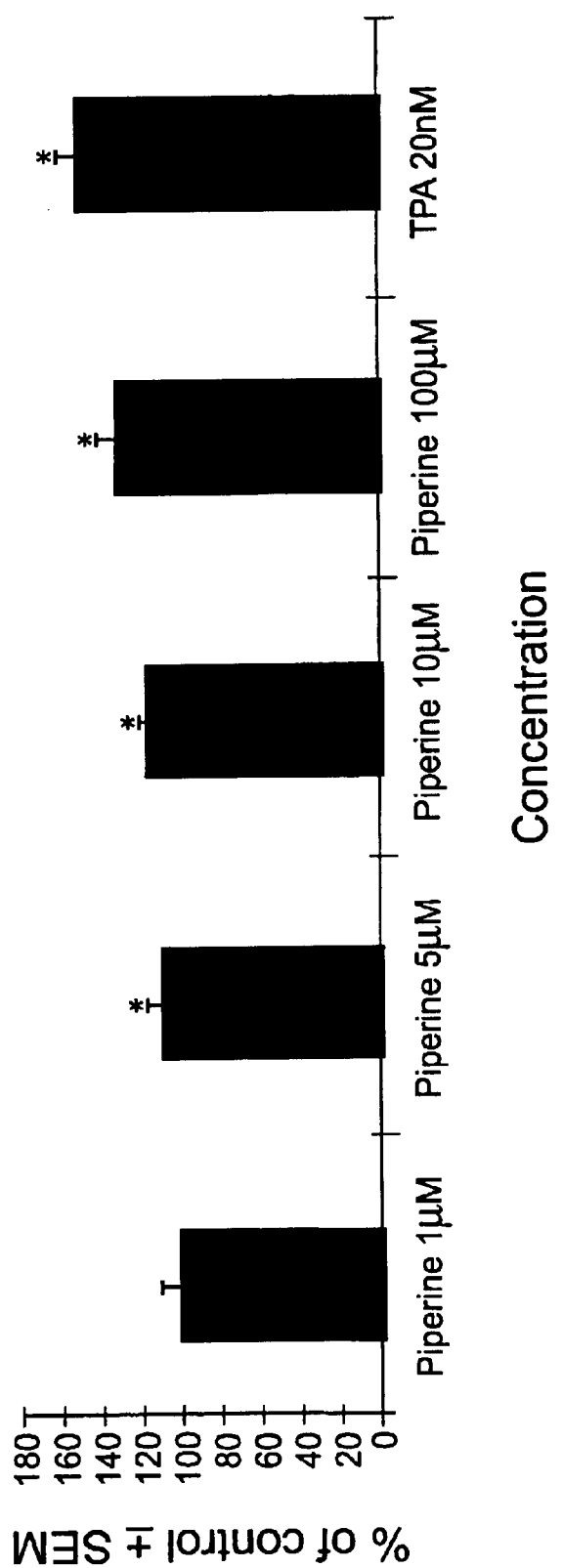
FIG. 6: Effects of piperine and TPA on the growth of human melanoblasts in the presence of ET3. *P<0.05 when compared to vehicle control (One way Anova, followed by Dunnett's t-test).

Results
FIG. 6 shows the effect of piperine on the growth of human melanoblasts in vitro. Piperine at the concentrations of 1, 10, 100 µM was found to cause significant stimulation to human melanoblasts in a dose response manner, with 34% more cell yield compared to vehicle control when the culture was exposed to 100 µM piperine in culture for 5 days. TPA, a well-known melanocytic growth-stimulating agent, was also able to cause significant cell growth at tested concentrations, with over 50% of more cell yield observed when the culture was exposed to 20 nM for 5 days. In the other repeated experiments, piperine was consistently observed to induce significant cell growth at the concentrations ranging from 5–100 µM; these stimulatory effects were generally less than that of TPA. Morphologically, in the presence of piperine, melanoblasts appeared to be more dendritic and the cell bodies were flatter and smaller.

Example 9
Experiments on Human Melanocytes in Culture

Human melanocytes used in this experiment were derived from induced differentiation of human foetal melanoblasts. The key character of human melanocytes that is different from its precursor melanoblasts is their ability to synthesise melanin. Melanin is a valid marker for melanocytes. The cell pellet of human melanocytes exhibits a characteristic brown to black colour, whereas human melanoblasts cannot produce melanin thus devoid of brown or black colour in the cell pellet.

Two protocols were employed for the experiments on human melanocytes in culture. The first employed 24-well plates and evaluated cell number with SRB assay. The second employed petri dishes and cell number was counted with a haemocytometer chamber.

For the first protocol, subconfluent human melanocytes maintained in a Ø100 mm petri dish were subcultured into two 24-well plates (Falcon) using basic culture medium of RPMI 1640 supplemented with FBS (10%), bFGF (100 pM), CT (1 nM) and endothelin 1 (1 nM). The initial plating density was 20,000 cells/cm² (38,200 cells/well) with each well containing 1000 µl medium. After incubation in a 10% $CO_2$, humidified atmosphere, at 37° C. for 2–3 hours to allow the attachment of the cells, piperine in 500 µl medium was added into wells to made up final concentrations of 0, 1, 5, 10 and 100 µM. Cells only in the medium with above supplement lacking of endothelin 1 were also set up as negative control. Six replicates were used in each group of treatment, and culture was incubated for 5 days before the cells were harvested by fixing with cold TCA (final concentration 20%) and processed with SRB assay. The solubilized SRB dye solution was transferred to a 96-well plate for optical density reading.

For the second protocol, subconfluent human melanocytes were subcultured in a Ø60 mm petri dishes (28 cm², Falcon) with RPMI 1640 basic medium supplemented with FBS (10%), CT (1 nM), bFGF (100 pM) and endothelin 1 (1 nM). The initial plating density was 10,000 cells/cm², with 5 ml medium per dish. Cells were incubated for 2–3 hours in 10% $CO_2$, humidified atmosphere, at 37° C., followed by addition of piperine solution in to the dishes, making the final concentrations of 0, 1, 5, 10 and 100 μM. Cells in the above supplemented medium lacking endothelin 1 were also set up as a negative control. Three dishes were used for each treatment and the culture was maintained for 5 days before cells were harvested with trypsinisation and counted with a haemocytometer chamber. For melanin production experiment, the harvested cells were centrifuged and pelleted. After carefully removing the medium, NaOH (1 M) was used to solubilized the cell pellets and optical density read at 475 nm in a Perkin-Elmer WV spectrophotometer (model UV/VIS Lambda 2). The melanin content was calculated by using a regression equation y=0.005+0.005x corresponding to the calibration curve for synthetic melanin.

Results

Figure 7:
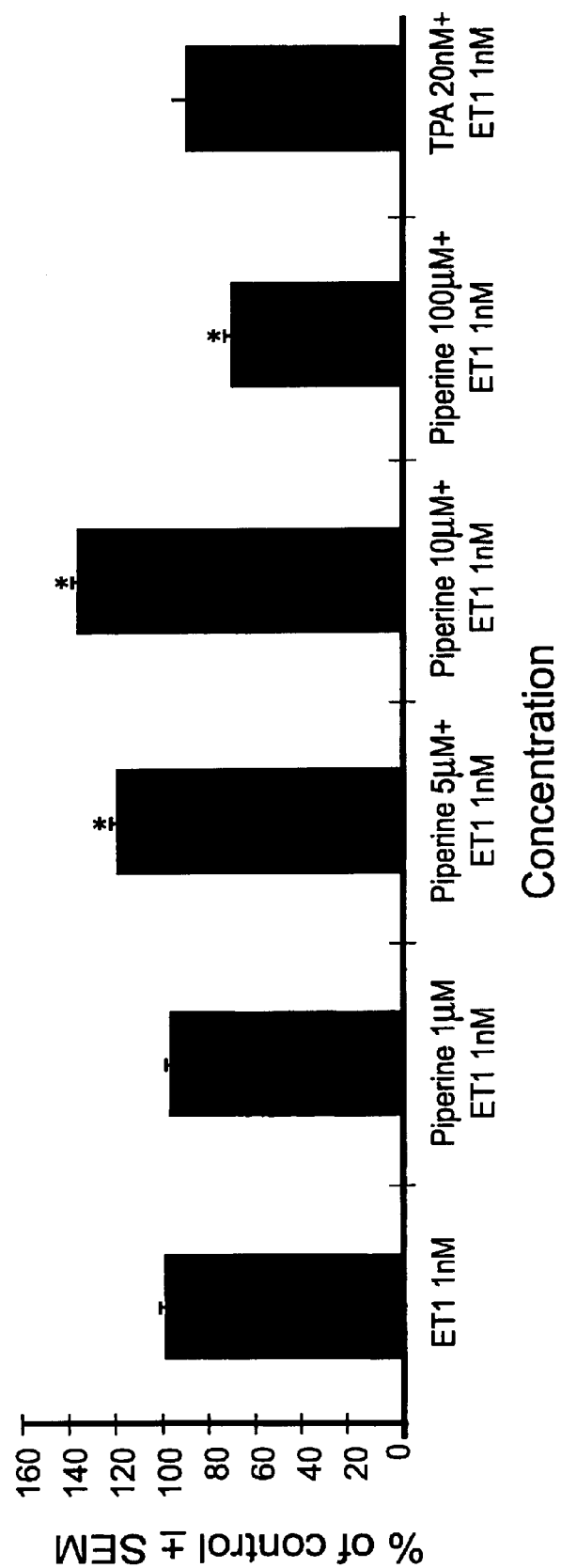
FIG. 7: Effects of piperine on the growth of human melanocytes in the presence of ET1. *P<0.05 when compared to ET1 1 nM treatment (One way Anova, followed by Dunnett's t-test).

FIG. 7 delineates the effects of piperine on the growth of human melanocytes cultured in 24-well plate. Piperine at the concentrations of 5 and 10 μM markedly stimulates the growth of these pigmented cells, with 36% more cells yielded when the culture was under the influence of 10 μM piperine for 5 days. However, at 100 μM, piperine exerted inhibitory effect on the growth of these cells. In addition, in the presence of 1 nM endothelin 1, TPA at 20 nM was not able to stimulate cell growth in our culture system, a result that is of great difference with that observed in human melanoblasts.

Table 5 shows the effects of piperine on the growth of human melanocytes cultured in petri dishes. It is conspicuous that in the presence of ET1 (1 nM), piperine at the concentrations of 5 and 10 μM significantly stimulated the growth of human melanocytes, with cell number over twice as many as that of ET1 (1 nM) control when this melanocyte cell type was exposed to 5 WM piperine for 5 days. This result was consistent with that obtained from the 24-well plate experiments, and it served to confirm that the stimulatory effects observed by SRB assay were indeed due to increased cell number rather than augmentation of protein production alone.

TABLE 1

Preliminary screening of 30 herbal aqueous extracts on the proliferation of melan-a cell line detected with SRB assay after 4 days culture.

| Names of herbs | Plant part | Cell number (% of control) after 4 days incubation when grown in the presence of extract at: | | |
| --- | --- | --- | --- | --- |
| | | 1 mg ml⁻¹ | 0.1 mg ml⁻¹ | 0.01 mg ml⁻¹ |
| plants with a significant stiinulatory effect | | | | |
| *Astragalus membranaceous* (Fisch.) Bunge | Root | 163.2* | 123.6* | 105.6 |
| *Citrus reticulata* Blanco (Qing Pi - unripe) | Peel | 16.0 | 138.5* | 127.6* |
| *Dictamnus dasycarpus* Turcz. | root bark | 105.0 | 159.4* | 98.0 |
| *Ophiopogon japonicus* (Thunb.) Kergawe | Root | 127.8 * | 126.5 * | 108.4 |
| *Piper nigrum* L. | Fruit | 11.5 | 215.4* | 151.3* |
| *Poria cocos* (Schw.) Wolf (fungus) | Sclerotium | 79.0 | 134.6* | 128.8* |
| *Tribulus terrestris* L. | Fruit | 80.7 | 136.1* | 142.2* |
| plants with no significant stimulatory effect | | | | |
| *Angelica daliurica* (Fisch.) Benth. & Hook. | Root | 50.4 | 118.3 | 107.0 |
| *Chaenomeles lagenaria* (Loisel.) Koldz. | fruit | 57.1 | 74.5 | 99.0 |
| *Citrus reticulata* Blanco (Chen Pi - ripe) | Peel | 34.6 | 101.1 | 81.1 |
| *Corydalis bulbosa* D.C. | Root | 91.8 | 101.2 | 92.9 |
| *Curcuma longa* L. | Root | 84.1 | 104.8 | 108.3 |
| *Cyperus rotundus* L. | Rhizome | 27.5 | 52.8 | 55.8 |
| *Cornus officinalis* Sieb. et Zucc. | Fruit | 30.4 | 92.1 | 101.6 |
| *Gentiana scabra* Bunge | Root | 42.2 | 107.4 | 108.6 |
| *Ligustrum lucidum* Ait. | Fruit | 97.6 | 58.1 | 98.4 |
| *Lithospermutn erythrorhizon* Sieb. et Zucc. | Root | 43.8 | 103.8 | 111.3 |
| *Notopteygium incisium* Ting | root/rhizome | 18.1 | 97.4 | 94.8 |
| *Paeonia lactiflora* Pall. | Root | 31.8 | 62.2 | 100.7 |
| *Paeonia suffruticosa* Andr. | Root | 53.2 | 72.0 | 132.8 |
| *Picrorhiza kurroa* Royle ex. Benth | Rhizome | 42.5 | 77.5 | 90.0 |
| *Platycodon grandiflorum* (Jacq.) A. DC. | Root | 35.1 | 94.1 | 96.8 |
| *Plumbago zeylanica* L. | Root | 30.2 | 103.9 | 114.1 |
| *Polygala tenuifolia* Willd. | Root | 12.7 | 43.7 | 79.6 |
| *Ramulus mari* (insect) | Whole | 41.1 | 87.1 | 89.4 |
| *Siesgesbeckia pubescens* Makirio | Herb | 17.0 | 40.8 | 51.7 |
| *Spirodela polyrrhiza* (L.) Scheid | Herb | 100 | 79.3 | 96.6 |
| *Trichosanthes kirilowii* Maxim | Root | 112.9 | 108.1 | 116.1 |
| *Tripterygium wilfordii* Hook. | Root | 89.8 | 36.7 | 63.3 |
| *Zingiber officinale* Roscoe | Rhizome | 7.9 | 105.8 | 90.6 |

*$P < 0.01$ compared with vehicle treatment (one-way ANOVA, followed by Dunnett's t-test).

TABLE 2

Effects of *Piper nigrum* extract on the proliferation of melan-a cells counted with haemocytometer

| Treatment to cells | cell number ($\times 10^{-4}$/ml) |
|---|---|
| Control | 2.02 |
| 20 nM TPA | 5.0* |
| *Piper nigrum* at 0.01 mg/ml | 3.06* |
| *Piper nigrum* at 0.1 mg/ml | 3.13* |

*$P < 0.01$ compared with vehicle treatment (one-way ANOVA, followed by Dunnett's t-test).

TABLE 3

Biological origin and the culture conditions of a panel of different cell types used in selectivily experiment.

| | | | optimum culture conditions | |
|---|---|---|---|---|
| Cell name | biological origin | FBS | Medium | incubation (4 days) |
| Melan-a | normal epidermal melanoblasts from embryos of inbred C57BL mice | 5% | RPMI1640 | 37° C., 10% $CO_2$ |
| Melan-c | albino embryos of outbred LAC-MF strain mice | 10% | RPMI1640 | 37° C., 10% $CO_2$ |
| FM2LE melanoblast | human foetal melanoblasts from epidermis (strain 21) | 10% | MCDB153 | 37° C., 10% $CO_2$ |
| FM21E melanocyte | Human melanocytes derived from FM2LE melanoblasts | | RPMI1640 | 37° C., 10% $CO_2$ |
| SVK14 | human keratinocytes | 10% | DMEM | 37° C., 10% $CO_2$ |
| CSM14.1.4 | neuronal cells from mesencephalin of rat | 10% | DMEM | 34° C., 5% $CO_2$ |
| SC1 | Fibroblastoids from neonatal murine skin | 10% | DMEM | 37° C., 10% $CO_2$ |
| XB2 | murine keratinocytes | 10% | DMEM | 37° C., 10% $CO_2$ |
| B6F10 | mouse melanoma | 5% | RPMI1640 | 37° C., 10% $CO_2$ |
| CAC02 | human colon cancer | 10% | RPMI1640 | 37° C., 10% $CO_2$ |
| IM9 | human lymphoblastoid B cells | 10% | RPMI1640 | 37° C., 5% $CO_2$ |
| Swiss 3T3 | mouse fibroblasls | 10% | DMDM | 37° C., 5% $CO_2$ |
| Human lymphocytes | healthy human blood samples | 10% | DMEM | 37° C., 5% $CO_2$ |

TABLE 4

Effects of piperine and TPA on the growth of a panel of cell types. (see Table 3 for details of cells)

| | cell number as a % of control | | | | | | |
|---|---|---|---|---|---|---|---|
| | piperine at the concentration of (μM) | | | | | TPA at the concentration of | |
| Cell type | 0.01 | 0.1 | 1 | 10 | 100 | 20 nM | 200 nM |
| Melan-a | ND | 130* | 169* | 153* | ND | 295* | ND |
| Melan-c | 109 | 208* | 198* | 119* | '137* | 186* | 222* |
| FM21E Melanoblast | ND | 101 | 101 | 119* | 134* | 153* | ND |
| FM21E human melanocytes | ND | ND | 98 | 143* | 75* | 98 | 102 |
| SVK14 | 97 | 101 | 92 | 84* | 23* | 71* | 66* |
| CSM14.1.4 | 93 | 94 | 95 | 89 | 64* | 85* | 76* |
| SC1 | 191* | 178* | 175* | 204* | 190* | 178* | 199* |
| XB2 | 80 | 90 | 86 | 90 | 42* | 96 | 99 |
| B16F10 | 71* | 64* | 47* | 33* | 0* | 35* | 55* |
| CACO2 | 103 | 99 | 102 | 81* | 34* | 95 | 90 |
| IM9 | ND | 101 | 103 | 69* | ND | ND | ND |
| Swiss 3T3 | 113 | 104 | 106 | 102 | 51* | 185* | 207* |
| human Lymphocytes | ND | 93 | 93 | ND | ND | 282* | ND |

*$P < 0.05$ compared to treatment with vehicle alone (one-way ANOVA followed by Dunnett's t-test);
ND = not done.
Relative standard deviations of all values were less than 10% of the mean

TABLE 5

Effects of piperine on the proliferation and melanin production of human melanocytes cultured in petri dishes

| Treatments | Cell no.(× $10^{-4}$) ± SD after cultured for 5 days | % of control (ET1 1 nM) | OD reading ± SD at 475 nm | Melanin content/$10^4$ cells |
|---|---|---|---|---|
| Cells only | 17.71 ± 6.16* | 49.1 | 0.026 ± 0.0049* | 0.23 ± 0.001 µg |
| ET1 (1 Nm) | 36.04 ± 6.16 | 100.0 | 0.087 ± 0.044 | 0.46 ± 0.01 µg |
| ET1 (1 nM) + piperine (1 µM) | 60.83 ± 16.78 | 168.8 | 0.134 ± 0.014* | 0.42 ± 0.03 µg |
| ET1 (1 nM) + piperine (5 µM) | 78.96 ± 5.63* | 219.1 | 0.137 ± 0.0085* | 0.334 ± 0.01 µg |
| ET1 (1 nM) + Piperine (10 µM) | 64.79 ± 13.47* | 179.8 | 0.139 ± 0.028* | 0.41 ± 0.07 µg |
| ET1 (1 nM) + piperine (100 µM) | 61.04 ± 10.04 | 169.4 | 0.144 ± 0.0046* | 0.46 ± 0.001 µg |

*$P < 0.05$ when compared to ET1 (1 nM) control (one way ANOVA, followed by Dunnett's t-test).

Example 10

Derivatives of Piperine 1.0 Introduction

Vitiligo is defined as a circumscribed, acquired, idiopathic, progressive hypomelanotic skin disorder which is characterised by the development of patchy depigmented macules due to progressive loss of melanocytes which is often familial with lack of established aetiology.

Various piperine derivatives of formula (1) were synthesised and tested for melanocyte (mouse melan-a) proliferant activity in-vitro. Cells were incubated with the test compound for 4 days, after which the sulphorhodamine-B (SRB) assay was performed to determine cell number SRB uptake was measured as optical density at 550 nm. The control assay was carried out on cells incubated without test compound. There were 2 or 3 series of experiments, each of which consisted of six replicate experiments. The results are tabulated below.

1.1 Percentage Cell Growth (A)

Percentage cell growth was obtained with a given compound calculated as (optical density in the presence of the compound/control optical density)×100.

1.2 Relative Activity to Piperine

Melan-a cell proliferant activity for tested compounds was compared with that obtained with piperine. Percentage stimulant activity is (A-100) where A stands for piperine or a test compound's percentage cell growth (see 1.1). All figures are given with Standard Error of Measurement.

Relative activity to piperine was calculated as (A-100) compound/(A-100) piperine).

Interpretation of the relative active value is as follows
<0—Inhibition of cell growth
0—No effect (equal to control)
0–1—Stimulant but weaker effect than pipeline
1—Equal stimulant effect to piperine
>1—Stimulant and stronger effect than piperine 1.3 Dendricity Effect on dendricity of melan-a cells by the test compounds was by observation under microscope. Dendricity is relevant to vitiligo since normal skin melanocytes have dendrites, but in vitiligo the melanocytes seem to lose these before they disappear from the patches.

1.4 Synthesis of Piperine Analogues

Analogues of piperine were synthesised using methods described in the literature, adapted from the literature or devised in the inventors' laboratory. Structures of compounds were verified using NMR, MS, IR spectroscopy and melting point. Unless a synthetic method is given, reagents and reactants were purchased from Sigma Aldrich.

1.5 Results

Figure 8:
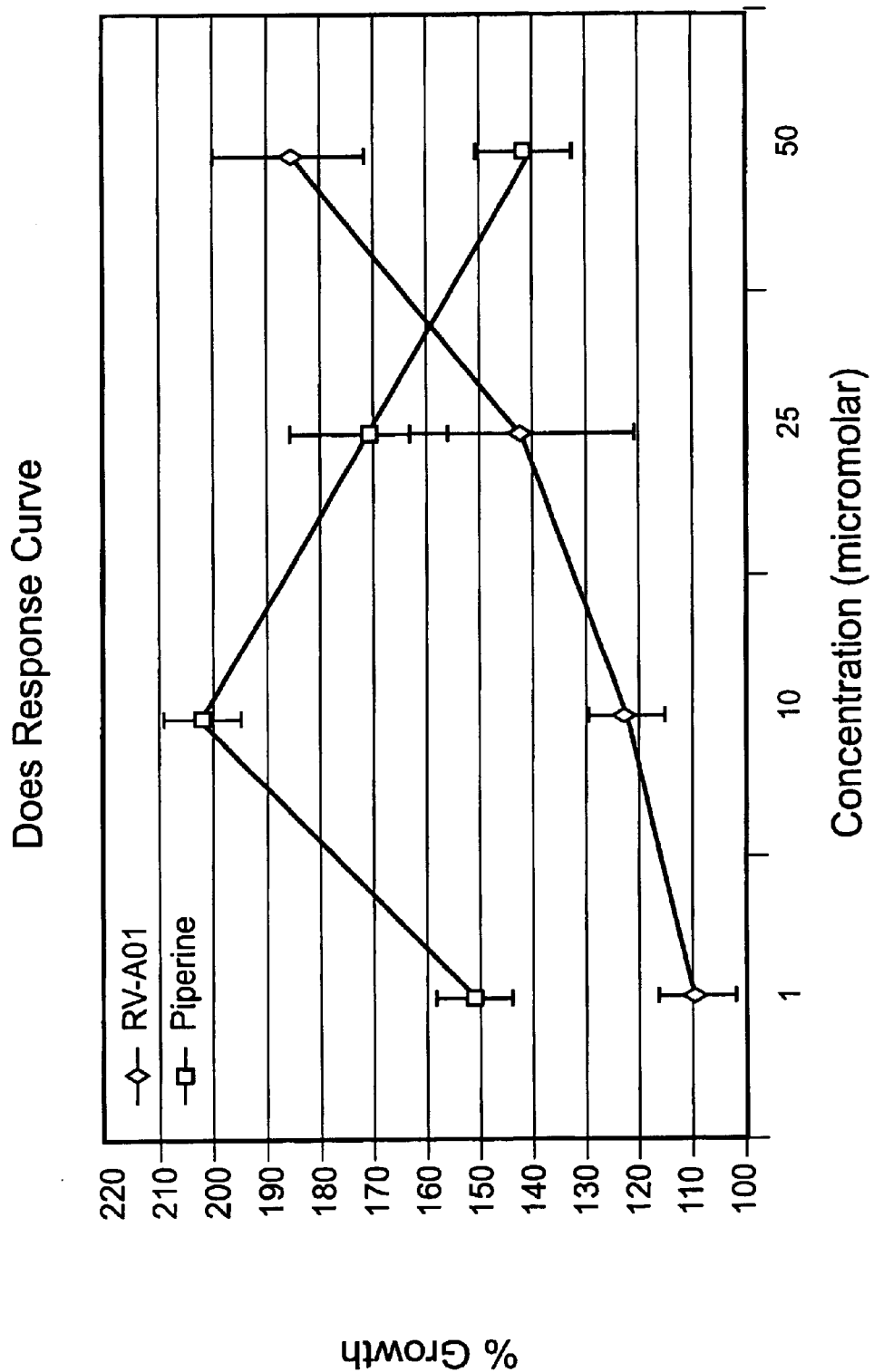
FIG. 8: Dose response curve showing the growth of melan-a cells in presence of a compound of formula (1), RV-A01, as % of control plotted against concentration.

Table 6 presents an overall summary of the results appearing in detail in other Tables which follow. Tables 7–12 relate to results at a single concentration of test compound (10 µM). They are followed by data showing results at other concentrations. Many compounds showed a "cross-over" effect in which the test compound was less active than piperine at 10 µM but more active at 50 µM. This is illustrated for one compound (RV-A01) in FIG. 8 of the Drawings.

TABLE 6

Overall Summary of Results

| Test CPD. | Change with Respect to Piperine | Active at 10 µM? | Active at higher conc. (µM)? | More active than piperine at higher conc. (µM)? |
|---|---|---|---|---|
| Vary amide (amino group listed below) | | | | |
| RV-A01 | Pyrrolidino | Yes | 25, 50 | 50 |
| RV-A02 | Morpholino | Yes | 25, 50 | 50 |
| RV-A04 | 3,4-methylenedioxy-benzylamino | Yes[a] | 50 | 50 |
| RV-A05 | Hexylamino | Yes | 25, 50 | No |
| RV-A06 | Isobutylamino | Yes | 25 | No |

TABLE 6-continued

Overall Summary of Results

| Test CPD. | Change with Respect to Piperine | Active at 10 μM? | Active at higher conc. (μM)? | More active than piperine at higher conc. (μM)? |
|---|---|---|---|---|
| RV-A07 | Methylamino | Yes | No | No |
| RV-A08 | Ethylamino | Yes | No | No |
| RV-A09 | Isopropylamino | Yes | No | No |
| RV-A10 | Cyclohexylamino | Yes | 50 | 50 |
| RV-A11 | Butylamino | Yes | 50 | 50 |
| Shorten connecting chain by 2 C-atoms (1 double bond) | | | | |
| RV-B01 | Piperidino | Yes | 25, 50 | 50 |
| Shorten connecting chain by 2 C-atoms (1 double bond) and vary amino part of amide group | | | | |
| RV-B02 | Pyrrolidino | No[b] | Not done[d] | Not done |
| RV-B03 | Morpholino | No | Not done[d] | Not done |
| Replace amide by ester (alkyl group listed below) | | | | |
| RV-AB1 | Methyl | Yes | 50, 100 | 50, 100 |
| RV-AB2 | Ethyl | No[c] | Not done | Not done |
| RV-AB4 | Isopropyl | Yes | 50 | 50 |
| RV-AB5 | Propyl | Yes | 50 | 50, 100 |
| RV-AB6 | Butyl | Yes | 50, 100 | 50, 100 |
| Shorten connecting chain as above and replace amide by ester (alkyl group listed below) | | | | |
| RV-BB1 | Methyl | No[b] | Not done | Not done |
| Reduce double bonds in connecting chain, making it saturated | | | | |
| RV-C02 | | Yes | 25, 50 | No |
| Reduce double bonds in connecting chain and shorten it by 2 C-atoms | | | | |
| RV-C03 | | No[b] | Not done | Not done |
| Replace 3',4'-methylenedioxy by methoxy and shorten connecting chain by 2 C-atoms (1 double bond) | | | | |
| RV-G01 | 6'-MeO | No | 100[e] | No |
| RV-G02 | 3'-MeO | No | 100[e] | No |
| RV-G03 | 4'-MeO | No | 100 | No |
| RV-G04 | 3',4'-Di-MeO | No | 100 | No |

Footnotes
[a]In dose response test.
[b]But the cells displayed weak dendricity suggestive of activity
[c]This result is considered anomalous. It is intended to re-run the experiment.
[d]Expected to show activity at 50 μM.
[e]Not corroborated by the t-test at 100 μM.

TABLE 7

| | | Effect on melan-a cells at μM concentration | | | | |
|---|---|---|---|---|---|---|
| Variation on Nitrogen Substituent of Piperine | | Percentage cell growth (Repeated experiments | | Stimulant activity | Relative activity to piperine | Den- dricity |
| Code N° | Structure | Test cpd. | Piperine | | | |
| RV-A01 | (structure) | 183 ± 34** 202 ± 84* | 180 ± 50** 191 ± 63* | Positive | 1.03 1.01 | +++ |
| RV-A02 | (structure) | 156 ± 58 187 ± 40** 153 ± 19** | 210 ± 65** 170 ± 22 155 ± 19** | Positive | 0.5 1.02 0.9 | +++ |

TABLE 7-continued

| | | Effect on melan-a cells at µM concentration | | | | |
|---|---|---|---|---|---|---|
| Variation on Nitrogen Substituent of Piperine | | Percentage cell growth (Repeated experiments | | Stimulant activity | Relative activity to piperine | Den-dricity |
| Code N° | Structure | Test cpd. | Piperine | | | |
| RV-A04 | [structure: piperine analog with N-piperonyl amide] | 149 ± 47<br>119 ± 27<br>147 ± 22 | 170 ± 39<br>169 ± 29<br>173 ± 28** | Non-significant here, but positive in dose response test | 0.7<br>0.27<br>.066 | + |
| RV-A05 | [structure: piperine analog with N-hexyl amide] | 166 ± 35<br>140 ± 17* | 170 ± 39<br>169 ± 29 | Positive | 0.93<br>0.57 | +++ |
| RV-A06 | [structure: piperine analog with N-isobutyl amide] | 147 ± 66<br>158 ± 24<br>156 ± 40 | 170 ± 39<br>169 ± 29<br>155 ± 18** | Positive | 1.69<br>0.83<br>1.0 | +++ |
| RV-A07 | [structure: piperine analog with N-methyl amide] | 170 ± 24* | 216 ± 33* | Positive | 0.6 | ++ |
| RV-A08 | [structure: piperine analog with N-ethyl amide] | 200 ± 14 | 236 ± 17 | Positive | 0.73 | +++ |
| RC-A09 | [structure: piperine analog with N-isopropyl amide] | 224 ± 19 | 263 ± 16** | Positive | 0.76 | +++ |
| RV-A10 | [structure: piperine analog with N-cyclohexyl amide] | 308 ± 29** | 302 ± 17** | Positive | 1.02 | +++ |
| RV-A11 | [structure: piperine analog with N-butyl amide] | 264 ± 21** | 347 ± 14** | Positive | 0.66 | +++ |

*P < 0.05, **P < 0.01 compared to vehicle treatment (Dunnett's test)

+++ highly dendritic, ++ moderately dendritic, + weakly dendritic, − no effect

TABLE 8

| | | Effect on melan-a cells at μM concentration | | | | |
|---|---|---|---|---|---|---|
| Variation in connecting chain length and amide group | | Percentage cell growth (Repeated experiments) | | Stimulant activity | Relative activity to piperine | Dendricity |
| Code N° | Structure | Test | Piperine | | | |
| RV-B01 | [structure: piperidine amide of methylenedioxycinnamoyl] | 171 ± 33<br>148 ± 20<br>152 ± 22 | 180 ± 50<br>191 ± 63<br>155 ± 18** | Positive | 0.88<br>0.52<br>0.97 | ++ |
| RV-B02 | [structure: pyrrolidine amide of methylenedioxycinnamoyl] | 140 ± 14<br>154 ± 33<br>135 ± 4 | 180 ± 50<br>191 ± 63<br>155 ± 18** | Non-significant | 0.2<br>0.59<br>0.63 | + |
| RV-B03 | [structure: morpholine amide of methylenedioxycinnamoyl] | 103 ± 12<br>116 ± 17 | 210 ± 65<br>170 ± 22 | None | 0.02<br>0.22 | – |

**$P < 0.01$ compared to vehicle treatment (Dunnett's t test)
++ moderately dendritic,
+ weakly dendritic,
– no effect

TABLE 9

| | | Effect on melan-a cells at μM concentration | | | | |
|---|---|---|---|---|---|---|
| Replacement of amide by ester group | | Percentage cell growth (Repeated experiments) | | Stimulant activity | Relative activity to piperine | Dendricity |
| Code N° | Structure | Test | Piperine | | | |
| RV-AB1 | [structure: methyl piperate] | 163 ± 38<br>141 ± 18*<br>151 ± 7* | 210 ± 65<br>170 ± 22<br>155 ± 18** | Positive | 0.57<br>0.59<br>0.93 | ++ |
| RV-AB2 | [structure: ethyl piperate] | 29 ± 9<br>22 ± 0.4 | 171 ± 39<br>171 ± 39 | Positive | −1<br>−1.09 | Toxic |
| RV-AB4 | [structure: isopropyl piperate] | 224 ± ** | 255 ± ** | Positive | 0.8 | ++ |
| RV-AB5 | [structure: propyl piperate] | 166 ± 35** | 169 ± 29** | Positive | 0.95 | ++ |

TABLE 9-continued

| | | Effect on melan-a cells at μM concentration | | | | |
|---|---|---|---|---|---|---|
| Replacement of amide by ester group | | Percentage cell growth (Repeated experiments) | | Stimulant activity | Relative activity to piperine | Dendricity |
| Code N° | Structure | Test | Piperine | | | |
| RV-AB6 | | 148 ± 18** | 181 ± 11** | Positive | 0.59 | + |

*P < 0.05,
**P < 0.01 compared to vehicle treatment (Dunnett's t test)
+++ highly dendritic,
++ moderately dendritic,
+ weakly dendritic,
− no effect

TABLE 10

| | | Effect on melan-a cells at μM concentration | | | | |
|---|---|---|---|---|---|---|
| Replacement of amide by ester group and variation in connecting chain length | | Percentage cell growth (Repeated experiments) | | Stimulant activity | Relative activity to piperine | Dendricity |
| Code N° | Structure | Test | Piperine | | | |
| RV-BB1 | | 149 ± 27<br>129 ± 15<br>121 ± 12 | 210 ± 65<br>170 ± 22<br>155 ± 18** | Non-sigmificant | 0.44<br>0.41<br>0.39 | + |

**P < 0.01 compared to vehicle treatment (Dunnett's t test),
++ moderately dendriticy

TABLE 11

| | | Effect on melan-a cells at μM concentration | | | | |
|---|---|---|---|---|---|---|
| Reduction of double bonds in connecting chain and variation in chain length | | Percentage cell growth (Repeated experiments) | | Stimulant activity | Relative activity to piperine | Dendricity |
| Code N° | Structure | Test | Piperine | | | |
| RV-C02 | | 169 ± 29<br>195 ± 89 | 180 ± 50<br>191 ± 63 | Positive | 0.8<br>1.04 | +++ |
| RV-C03 | | 104 ± 5<br>113 ± 2 | 171 ± 7<br>171 ± 7 | None | 0.056<br>0.18 | + |
| RV-C04 | | 192 ± 5** | 216 ± 18** | Positive | 0.79 | +++ |

TABLE 11-continued

| | | Effect on melan-a cells at μM concentration | | | | |
|---|---|---|---|---|---|---|
| Reduction of double bonds in connecting chain and variation in chain length | | Percentage cell growth (Repeated experiments) | | Stimulant activity | Relative activity to piperine | Dendricity |
| Code N° | Structure | Test | Piperine | | | |
| RV-C05 | 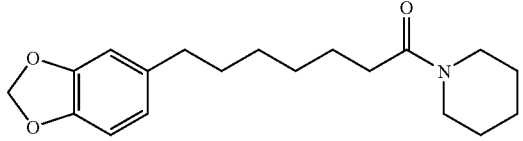 | 160 ± 5 | 192 ± 2 | Positive | 0.65 | ++ |

** $P < 0.01$ compared to vehicle treatment (Dunnett's t test)
+++ highly dendritic,
+ weakly dendritic,
− no effect

TABLE 12

| | | Effect on melan-a cells at μM concentration | | | | |
|---|---|---|---|---|---|---|
| Variation in the phenyl substituent and connecting chain length | | Percentage cell growth (Repeated experiments) | | Stimulant activity | Relative activity to piperine | Dendricity |
| Code N° | Structure | Test | Piperine | | | |
| RV-G01 | 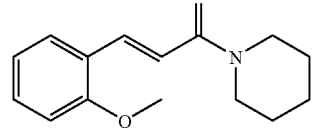 | 105 ± 8 | 202 ± 29** | None | 0.04 | |
| RV-G02 | 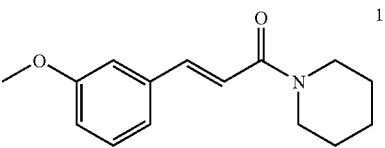 | 119 ± 18<br>87 ± 17 | 171 ± 39<br>171 ± 7 | Negative | 0.26<br>−0.18 | − |
| RV-G03 | 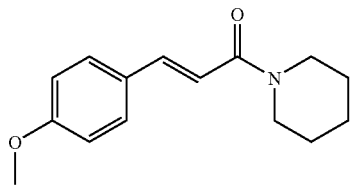 | 121 ± 8<br>122 ± 8* | 171 ± 39<br>171 ± 7 | Non-significant | 0.29<br>0.30 | − |
| RV-G04 | 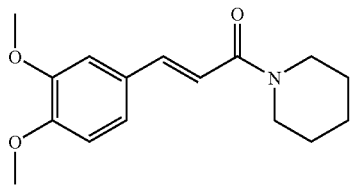 | 100 ± 9 | 224 ± 11** | None | 0 | − |

* $P < 0.05$,
** $P < 0.01$ compared to vehicle treatment (Dunnett's t test)
− no effect

| Code N° | Structure |
|---|---|
| RV-A01 | 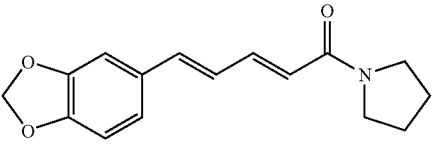 |

| Compounds Tested | 1 µM | 10 µM | 25 µM | 50 µM |
|---|---|---|---|---|
| Piperine | 151 ± 7**♦ | 202 ± 12**♦ | 171 ± 15**♦ | 142 ± 9** |
| RV-A01 | 109 ± 7 | 122 ± 7 | 142 ± 21** | 186 ± 14** |

**P < 0.01 Compared to vehicle treatment (Dunnet's t test)
*P < 0.05 Compared to vehicle treatment (Dunnet's t test)
♦Piperine is significantly more active than test compound P < 0.05
Test compound is significantly more active than Piperine P < 0.05

| Code N° | Structure |
|---|---|
| RV-A04 | 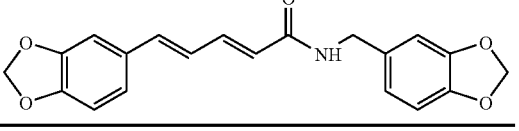 |

| Compounds Tested | 1 µM | 10 µM | 50 µM | 100 µM |
|---|---|---|---|---|
| Piperine | 120 ± 11 | 178 ± 11**♦ | 116 ± 13 | 92 ± 9 |
| RV-A04 | 101 ± 12 | 138 ± 10** | 150 ± 15** | 71 ± 9 |
| Dentricity RV-A04 | − | + | + | |

**P < 0.01 Compared to vehicle treatment (Dunnet's t test)
*P < 0.05 Compared to vehicle treatment (Dunnet's t test)
♦Piperine is significantly more active than test compound P < 0.05
Test compound is significantly more active than Piperine P < 0.05
− no effect,
+ wealdy dendritic,
++ moderately dendritic

| Code N° | Structure |
|---|---|
| RV-A05 | 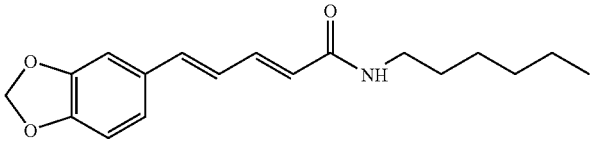 |

| Compounds Tested | 1 µM | 1 µM | 25 µM | 5 µM |
|---|---|---|---|---|
| Piperine | 173 ± 6**♦ | 230 ± 13**♦ | 188 ± 19** | 182 ± 15** |
| RV-A05 | 155 ± 9** | 188 ± 13** | 178 ± 18** | 174 ± 8** |

**P < 0.01 Compared to vehicle treatment (Dunnet's t test)
♦Piperine is significantly more active than test compound P < 0.05

| Code N° | Structure |
|---|---|
| RV-A02 | 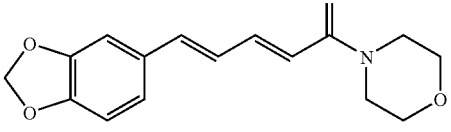 |

| Compounds Tested | 1 µM | 10 µM | 25 µM | 50 µM |
|---|---|---|---|---|
| Piperine | 147 ± 11**♦ | 192 ± 13**♦ | 167 ± 19** | 142 ± 15** |
| RV-A02 | 125 ± 10 | 167 ± 17** | 171 ± 8** | 168 ± 12** |

**P < 0.01 Compared to vehicle treatment (Dunnet's t test)
♦Piperine is significantly more active than test compound P < 0.05
Test compound is significantly more active than Piperine P < 0.05

| Code N° | Structure |
|---|---|
| RV-A06 | 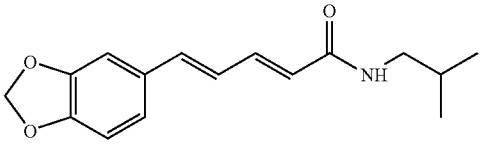 |

| Compounds Tested | 1 µM | 10 µM | 25 µM | 5 µM |
|---|---|---|---|---|
| Piperine | 147 ± 8♦ | 195 ± 22** | 173 ± 17* | 159 ± 14 |
| RV-A06 | 134 ± 7 | 188 ± 14** | 172 ± 15* | 135 ± 24 |

**P < 0.01 Compared to vehicle treatment (Dunnet's t test)
*P < 0.05 Compared to vehicle treatment (Dunnet's t test)
♦Piperine is significantly more active than test compound P < 0.05

| Code N° | Structure |
|---|---|
| RV-A07 | (3,4-methylenedioxyphenyl)-penta-2,4-dienoic acid N-methylamide |

| Compounds Tested | 1 μM | 10 μM | 50 μM | 100 μM |
|---|---|---|---|---|
| Piperine | 211 ± 16**◆ | 216 ± 33** | 52 ± 15 | 16 ± 3 |
| RV-A07 | 140 ± 12** | 170 ± 24** | 71 ± 5 | 46 ± 2 |
| Dentricity of RV-A07 | ++ | ++ | + | + |

**$P < 0.01$ Compared to vehicle treatment (Dunnet's t test)
◆Piperine is significantly more active than test compound $P < 0.05$
++ moderately dendritic,
+ weakly dendritic

| Code N° | Structure |
|---|---|
| RV-A08 | (3,4-methylenedioxyphenyl)-penta-2,4-dienoic acid N-ethylamide |

| Compounds Tested | 1 μM | 10 μM | 50 μM | 100 μM |
|---|---|---|---|---|
| Piperine | 216 ± 14**◆ | 236 ± 17** | 61 ± 11 | 32 ± 5 |
| RV-A08 | 139 ± 27** | 200 ± 14** | 81 ± 12 | 62 ± 13 |
| Dendricity of RV-A08 | ++ | +++ | + | + |

**$P < 0.01$ Compared to vehicle treatment (Dunnet's t test)
◆Piperine is significantly more active than test compound $P < 0.05$
+++ highly dendritic,
++ moderately dendritic,
+ weakly dendritic

| Code N° | Structure |
|---|---|
| RV-A09 | (3,4-methylenedioxyphenyl)-penta-2,4-dienoic acid N-isopropylamide |

| Compounds Tested | 1 μM | 10 μM | 50 μM | 100 μM |
|---|---|---|---|---|
| Piperine | 221 ± 17**◆ | 263 ± 16** | 77 ± 12 | 24 ± 2 |
| RV-A09 | 187 ± 15** | 224 ± 19** | 85 ± 5 | 42 ± 6 |
| Dendricity of RV-A09 | +++ | +++ | + | + |

**$P < 0.01$ Compared to vehicle treatment (Dunnet's t test)
◆Piperine is significantly more active than test compound $P < 0.05$
+++ highly dendritic,
+ weakly dendritic

| Code N° | Structure |
|---|---|
| RV-A10 | (3,4-methylenedioxyphenyl)-penta-2,4-dienoic acid N-cyclohexylamide |

| Compounds Tested | 1 μM | 10 μM | 50 μM | 100 μM |
|---|---|---|---|---|
| Piperine | 236 ± 30** | 302 ± 17** | 78 ± 11 | 21 ± 4 |
| RV-A10 | 301 ± 20** | 308 ± 29** | 155 ± 22** | 100 ± 13 |
| Dendricity of RV-A10 | +++ | +++ | ++ | + |

**$P < 0.01$ Compared to vehicle treatment (Dunnet's t test)
Compound is significantly more active than piperine $P < 0.05$
+++ highly dendritic,
++ moderately dendritic,
+ weakly dendritic

| Code N° | Structure |
|---|---|
| RV-A11 | (3,4-methylenedioxyphenyl)-penta-2,4-dienoic acid N-butylamide |

| Compounds Tested | 1 μM | 10 μM | 50 μM | 100 μM |
|---|---|---|---|---|
| Piperine | 251 ± 19**◆ | 347 ± 14** | 61 ± 7 | 25 ± 2 |
| RV-A11 | 189 ± 6** | 264 ± 21** | 158 ± 20** | 84 ± 6 |
| Dendricity of RV-A11 | +++ | +++ | ++ | + |

**$P < 0.01$ Compared to vehicle treatment (Dunnet's t test)
◆Piperine is significantly more active than test compound $P < 0.05$
Compound is significantly more active than Piperine $P < 0.05$

| Code N° | Structure |
|---|---|
| RV-B01 | (3,4-methylenedioxyphenyl)-acryloyl piperidine |

| Compounds Tested | 1 μM | 10 μM | 25 μM | 50 μM |
|---|---|---|---|---|
| Piperine | 144 ± 27**◆ | 190 ± 7** | 172 ± 11** | 153 ± 10** |
| RV-B01 | 111 ± 6 | 147 ± 7** | 187 ± 18** | 187 ± 8** |

**$P < 0.01$ Compared to vehicle treatment (Dunnet's t test)
◆Piperine is significantly more active than test compound $P < 0.05$
Compound is significantly more active than Piperine $P < 0.05$

| Code N° | Structure |
|---|---|
| RV-AB1 | (methyl ester of piperic acid, methylenedioxyphenyl-CH=CH-CH=CH-C(=O)-O-CH₃) |

| Compounds Tested | 1 μM | 10 μM | 50 μM | 100 μM |
|---|---|---|---|---|
| Piperine | 133 ± 31** | 177 ± 14**◆ | 139 ± 16* | 95 ± 24 |
| RV-AB1 | 125 ± 13 | 147 ± 16** | 187 ± 12** | 171 ± 8** |
| Dendricity of RV-AB1 | − | + | ++ | ++ |

**$P < 0.01$ Compared to vehicle treatment (Dunnet's t test)
*$P < 0.05$ compared to vehicle treatment (Dunnett's t test)
◆Piperine is significantly more active than test compound $P < 0.05$
Compound is significantly more active than Piperine $P < 0.05$
− no effect,
+ weakly dendritic,
++ moderately dendritic

| Code N° | Structure |
|---|---|
| RV-AB4 | (isopropyl ester of piperic acid) |

| Compounds Tested | 1 μM | 10 μM | 50 μM | 100 μM |
|---|---|---|---|---|
| Piperine | 223 ± 18**◆ | 255 ± 15** | 60 ± 16 | 24 ± 6 |
| RV-AB4 | 175 ± 6** | 224 ± 12** | 148 ±19** | 90 ± 7 |
| Dendricity of RV-AB4 | ++ | ++ | ++ | + |

**$P < 0.01$ Compared to vehicle treatment (Dunnet's t test)
◆Piperine is significantly more active than test compound $P < 0.05$
Compound is significantly more active than Piperine $P < 0.05$
++ moderately dendritic,
+ weakly dendritic

| Code N° | Structure |
|---|---|
| RV-AB5 | (propyl ester of piperic acid) |

| Compounds Tested | 1 μM | 10 μM | 50 μM | 100 μM |
|---|---|---|---|---|
| Piperine | 141 ± 26**◆ | 220 ± 29**◆ | 45 ± 12 | 23 ± 4 |
| RV-AB5 | 120 ± 21 | 151 ± 19** | 163 ± 8** | 123 ± 8 |
| Dendricity of RV-AB5 | − | ++ | ++ | + |

**$P < 0.01$ Compared to vehicle treatment (Dunnet's t test)
◆Piperine is significantly more active than test compound $P < 0.05$
Compound is significantly more active than Piperine $P < 0.05$
++ moderately dendritic,
+ weakly dendritic

| Code N° | Structure |
|---|---|
| RV-AB6 | (butyl ester of piperic acid) |

| Compounds Tested | 1 μM | 10 μM | 50 μM | 100 μM |
|---|---|---|---|---|
| Piperine | 113 ± 10 | 181 ± 11** | 43 ± 6 | 23 ± 6 |
| RV-AB6 | 103 ± 5 | 148 ± 18** | 190 ± 11** | 128 ± 17** |
| Dendricity of RV-AB6 | − | + | ++ | + |

**$P < 0.01$ Compared to vehicle treatment (Dunnet's t test)
Compound is significantly more active than Piperine $P < 0.05$
++ moderately dendritic,
+ weakly dendritic,
− no effect

| Code N° | Structure |
|---|---|
| RV-C02 | (methylenedioxyphenyl-(CH₂)₄-C(=O)-N-piperidine) |

| Compounds Tested | 1 μM | 10 μM | 25 μM | 50 μM |
|---|---|---|---|---|
| Piperine | 158 ± 10**◆ | 203 ± 11** | 188 ± 12** | 164 ± 6** |
| RV-C02 | 134 ± 15** | 183 ± 33** | 199 ± 31** | 175 ± 12** |

**$P < 0.01$ Compared to vehicle treatment (Dunnet's t test)
◆Piperine is significantly more active than test compound $P < 0.05$

| Code N° | Structure |
|---|---|
| RV-C04 | (methylenedioxyphenyl-(CH₂)₄-C(=O)-NH-cyclohexyl, with atom numbering 1–11 and 1′–6′) |

| Compound | 1 μM | 10 μM | 50 μM | 100 μM |
|---|---|---|---|---|
| Piperine | 191 ± 12**◆ | 216 ± 18** | 184 ± 6** | 96 ± 6 |
| RV-C04 | 129 ± 6** | 192 ± 6** | 192 ± 10** | 191 ± 12** |
| Dendricity of RV-C04 | + | +++ | +++ | +++ |

| RV-C05 | | | | |
|---|---|---|---|---|
| Code N° | Structure | | | |
| RV-C05 | 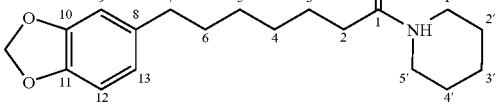 | | | |
| Compound | 1 µM | 10 µM | 50 µM | 100 µM |
| Piperine | 161 ± 13** | 192 ± 2**♦ | 189 ± 15** | 87 ± 13 |
| RV-C05 | 118 ± 1 | 160 ± 5**♦ | 158 ± 19** | 113 ± 15 |
| Dendricity of RV-C05 | + | ++ | ++ | + |

| Code N° | Structure | | | |
|---|---|---|---|---|
| RV-G01 | 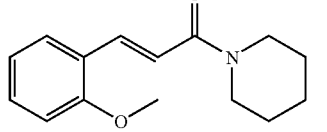 | | | |
| Compounds Tested | 1 µM | 10 µM | 50 µM | 100 µM |
| Piperine | 161 ± 23** | 202 ± 29** | 61 ± 5 | 40 ± 7 |
| RV-G01 | 99 ± 8 | 105 ± 8 | 103 ± 6 | 119 ± 9 |
| Dendricity of RV-G01 | – | – | – | – |

**P < 0.01 Compared to vehicle treatment (Dunnet's t test)
– no effect

| Code N° | Structure | | | |
|---|---|---|---|---|
| RV-G02 | 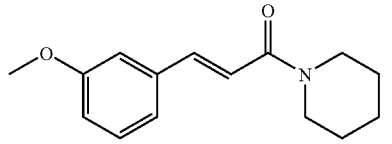 | | | |
| Compounds Tested | 1 µM | 10 µM | 50 µM | 100 µM |
| Piperine | 151 ± 17** | 201 ± 15** | 57 ± 15 | 39 ± 11 |
| RV-G02 | 99 ± 5 | 95 ± 18 | 110 ± 11 | 127 ± 9 |
| Dendricity of RV-G02 | – | – | – | – |

**P < 0.01 Compared to vehicle treatment (Dunnet's t test)
– no effect

| Code N° | Structure | | | |
|---|---|---|---|---|
| RV-G03 | 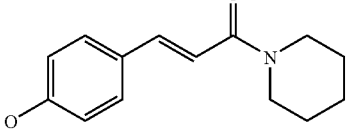 | | | |
| Compounds Tested | 1 µM | 10 µM | 50 µM | 100 µM |
| Piperine | 163 ± 9** | 181 ± 23** | 59 ± 11 | 40 ± 12 |
| RV-G03 | 90 ± 10 | 108 ± 20 | 111 ± 10 | 133 ± 15** |
| Dendricity of RV-G03 | – | – | – | – |

**P < 0.01 Compared to vehicle treatment (Dunnet's t test)
– no effect

| Code N° | Structure | | | |
|---|---|---|---|---|
| RV-G04 | 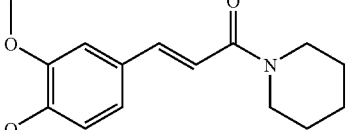 | | | |
| Compounds Tested | 1 µM | 10 µM | 50 µM | 100 µM |
| Piperine | 179 ± 12** | 224 ± 11** | 92 ± 19 | 35 ± 4 |
| RV-G04 | 95 ± 11 | 100 ± 9 | 114 ± 8 | 123 ± 7* |
| Dendricity of RV-G04 | – | – | – | – |

**P < 0.01 Compared to vehicle treatment (Dunnet's t test)
– no effect

2. Synthesis of Amide Derivatives of Piperinic Acid 2.1 Preparation of Piperinic Acid (RV-A00)

To piperine (1) (2 g, 0.7 mmol, 1 eq), 20% of methanolic KOH (100 ml) was added and refluxed for 2 days. After completion of the hydrolysis, methanol was removed under reduced pressure and a yellow coloured oily solid was obtained. This residue was dissolved in water (50 ml) and acidified with 6N HCl to pH <1 yielding a yellowish precipitate of piperinic acid. Recrystallization from methanol gave yellow needles (0.9 g, 60% yield). m.p. 206°–208° C. (Lit m.p. 217 °–218° C.)[1]

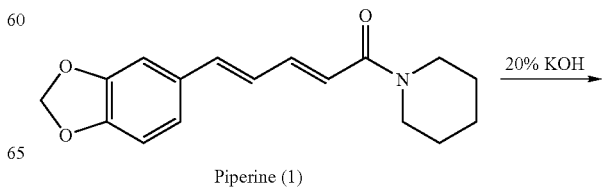

Piperine (1)

-continued

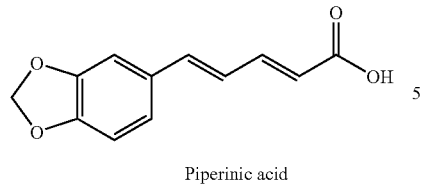

Piperinic acid

2.2 Synthesis of Piperlonguminine (RV-A06)

A mixture of piperinic acid (350 mg, 0.0016 mole, 1 eq) and triethylamine (0.4 ml, 0.0032 mole, 2 eq) in dichloromethane (50 ml) was stirred for 15 min at 0° C. To this mixture methanesulfonyl chloride (0.18 ml, 0.0024 mole, 1.5 eq) was added and stirred for further 30 min at 0° C. Isobutylamine (0.23 ml, 0.0024 mole, 1.5 eq) was added to the mixture and stirred for 1 h at 0° C. and 2 h at room temperature. Dichloromethane (50 ml) was added to the mixture which was then washed with 5% HCl (3×100 ml), saturated aqueous $NaHCO_3$ (3×100 ml) and water (3×100 ml). The organic fraction was dried over anhydrous sodium sulphate, filtered and rotary evaporated to yield a yellowish solid residue. Recrystallisation from methanol yielded colourless needles of piperlonguminine (120 mg, 32% yield) [2]. The reaction is presumed to proceed through a mesylate ester intermediate.

Piperlonguminine (RV-A06)

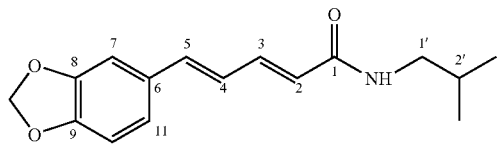

$^1$H-NMR ($CDCl_3$) δ: 5.96 (d, 1H, J=14.8, CH=CH—CH=CH), 7.36 (d,d, 1H, J=10.5, 14.8, CH=CH—CH=CH), 6.66 (d,d, 1H, J=15.4, 10.5, CH=CH—CH=CH), 6.76 (d, 1H, J=15.4 CH=CH—CH=CH), 6.96 (d, 1H J=1.6, Ar-7H), 6.76 (d, 1H J=8.0, Ar-10H), 6.87 (d, d, 1H J=1.6, 8.0 Ar-11H), 5.97 (s, 2H, O—$CH_2$—O), 3.18 (t, 2H, J=6.5 $CH_2$—CH), 1.83 (m, 1H, J=6.5 $CH_2$—CH), 0.94 (d, 6H, J=6.5, $(CH_3)_2$), 5.82 (t, 1H, NH J=5.3) $^{13}$C-NMR ($CDCl_3$): 20.4 ($CH_3$), 29.4 (CH), 47.3 ($CH_2$), 102.2 ($CH_2$), 106.2 (CH), 109.1 (CH), 123.3 (CH), 125.5 (CH), 126.0 (CH), 132.0 (C), 138.0 (CH), 140.4 (CH), 148.9 (C), 149.2 (C), 166.2 (C) MS m/z (%): 273 ($M^+$ 98), 216 (20), 201 (100), 174 (25), 173 (65), 172 (23), 171 (17) 143 (20), 115 (40), 96 (11). IR (KBr): $v_{max}$ (carbonyl group) 1644 m.p. 161.2°–161.7° C. (Lit m.p. 156°–160° C.)[1]

2.3 Synthesis of Other Amide Derivatives of Piperinic Acid

The general method was as for piperlonguminine (section 1.2), using the same proportions of reactive amine, triethylamine and methanesulfonyl chloride relative to piperinic acid (200 or 300 mg., 1 eq). Recrystallisation from ethyl acetate/petroleum spirit yielded the other amide derivatives of piperinic acid.

5-E,E-piperinoylpyrrolidine (RV-A01)

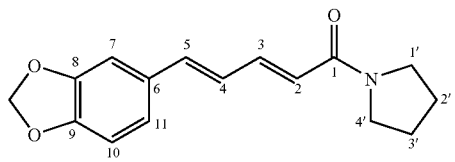

$^1$H-NMR ($CDCl_3$) δ: 6.26 (d, 1H, J=14.7, CH=CH—CH=CH), 7.43 (d,d, 1H, J=9.5, 14.7, CH=CH—CH=CH), 6.73 (d,d, 1H, J=15.3, 9.5, CH=CH—CH=CH), 6.78 (d, 1H, J=15.3 CH=CH—CH=CH), 6.98 (d,1H J=1.6, Ar-7-H), 6.77 (d,1H J=8.0, Ar-10-H), 6.89 (d, d, 1H J=1.6, 8.0 Ar-11-H), 5.97 (s, 2H, O—$CH_2$—O), 3.57 (t, 2H, J=4.0 N—$CH_2$ (pyrrolidine)) 3.54 (t, 2H, J=4.0 N—$CH_2$ (pyrrolidine)) 1.90 (m, 2H, $CH_2CH_2$(pyrrolidine)) 1.87 (m, 2H, $CH_2CH_2$(pyrrolidine)) $^{13}$C-NMR ($CDCl_3$): 24.3 ($CH_2$), 26.1 ($CH_2$), 45.9 ($CH_2$), 46.4 ($CH_2$), 101.2 ($CH_2$), 105.7 (CH), 108.4 (CH), 121.4 (CH), 122.5 (CH), 125.2 (CH), 130.9 (C), 138.7 (CH), 141.7 (CH), 148.1 (C), 148.2 (C), 164.9 (C) MS m/z (%): 271 ($M^+$ 78), 201 (100), 173 (30), 172 (15), 171 (13) 143 (13), 115 (27) IR (KBr): $v_{max}$ (carbonyl group) 1637 m.p. 142.9°–143° C. (Lit m.p. 142°–143° C.)[2], yield 49.2%

5-E,E-piperinoyl morpholine (RV-A02)

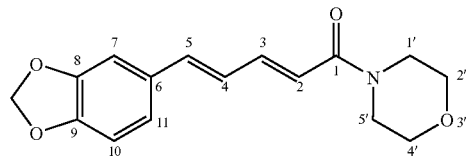

$^1$H-NMR ($CDCl_3$) δ: 6.37 (d, 1H, J=14.6, CH=CH—CH=CH), 7.45 (d,d, 1H, J=10.2, 14.6, CH=CH—CH=CH), 6.72 (d,d, 1H, J=15.5, 10.2, CH=CH—CH=CH), 6.79 (d, 1H, J=15.5 CH=CH—CH=CH), 6.98 (d, 1H J=1.5, Ar-7-H), 6.80 (d, 1H J=8.0, Ar-10-H), 6.89 (d, d, 1H J=1.5, 8.0 Ar-11-H), 5.98 (s, 2H, O—$CH_2$—O), 3.70 (t, 2H, J=4.0 $CH_2$—N—$CH_2$ (morpholine)) 3.60 (t, 2H, J=4.0 $CH_2$—O—$CH_2$ (morpholine)) $^{13}$C-NMR ($CDCl_3$): 42.3 ($CH_2$), 46.1($CH_2$), 66($CH_2$), 66($CH_2$), 101.3 ($CH_2$), 106.5 (CH), 108.5 (CH), 118.7 (CH), 122.7 (CH), 124.9 (CH), 130.8 (C), 139.1 (CH), 143.4 (CH), 148.2 (C), 148.3 (C), 165.6 (C) MS m/z (%): 287 ($M^+$ 57), 201 (100), 173 (25), 171 (10) 143 (10), 115 (30) IR (KBr): $v_{max}$ (carbonyl group) 1641 m.p. 161.8°–162.5° C. (Lit m.p. 167–168° C.)[3], yield 44.1%

5-E,E-piperinoylpiperinolymine (RV-A04)

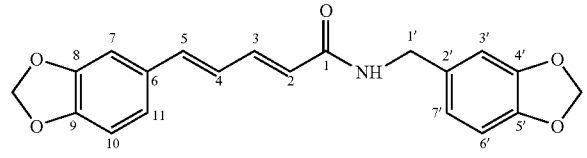

$^1$H-NMR ($CDCl_3$) δ: 5.98(d, 1H, J=14.9, CH=CH—CH=CH), 7.34 (d,d, 1H, J=10.7, 14.9, CH=CH—CH=CH), 6.73 (d,d, 1H, J=15.5, 10.7, CH=CH—CH=CH), 6.79 (d, 1H, J=15.5 CH=CH—CH=CH), 6.98 (d,2H J=1.5, Ar-7,3'-H), 6.78 (d,2H J=8.0, Ar-10,6'-H), 6.89 (d, d, 2H J=1.6, 8.0 Ar-11,7'-H), 5.98 (s, 2H, O—$CH_2$—O), 5.93 (s, 2H, O—$CH_2$—O), 4.40 (d, 2H, $CH_2$) 3.57 (br, 1H, NH) $^{13}$C-NMR ($CDCl_3$): 43.4 ($CH_2$), 101.1 ($CH_2$), 101.4

(CH$_2$), 105.8 (CH), 108.3 (CH) 108.5 (CH), 108.6 (CH), 121.2 (CH), 122.8 (CH), 124.7 (CH), 130.9 (C), 132.2 (C) 139.9 (CH), 141.6 (CH), 147.0 (C) 147.9 (C) 148.3 (C), 148.4 (C), 166.9 (C) MS m/z (%): 351 (M$^+$ 81), 216 (15), 203 (12), 202 (53) 201 (29), 174 (31), 173 (22), 150 (23) 144 (11), 143 (10), 135 (100), 116 (12) 115 (29) m.p. 190.5°–191.7° C., yield 50.1%

5-E,E-piperinoylhexylamine RV-A05

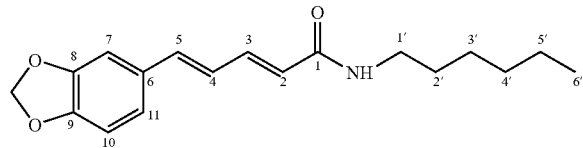

$^1$H-NMR (CDCl$_3$) δ: 5.90 (d, 1H, J=14.8, CH=CH—CH=CH), 7.35 (d,d, 1H, J=10.6, 14.8, CH=CH—CH=CH), 6.66 (d,d, 1H, J=15.4, 10.6, CH=CH—CH=CH), 6.76 (d, 1H, J=15.4 CH=CH—CH=CH), 6.97 (d,1H J=1.4, Ar-7H), 6.77 (d,1H J=8.0, Ar-10H), 6.88 (d, d, 1H J=1.5, 8.0 Ar-11H), 5.97 (s, 2H, O—CH$_2$—O), 3.34 (q, 2H, CH$_2$—CH$_2$—CH$_2$—CH$_2$—CH$_2$) 1.54 (m, 2H, CH$_2$—CH$_2$—CH$_2$—CH$_2$), 1.32 (m, 6H, CH$_2$—CH$_2$—CH$_2$—CH$_2$—CH$_2$) 0.88 (t, 3H, CH$_3$), 5.54 (br, NH) $^{13}$C-NMR (CDCl$_3$): 14.3 (CH$_3$), 22.5 (CH$_2$), 26.6 (CH$_2$), 29.6 (CH$_2$), 31.5 (CH$_2$), 39.7 (CH$_2$), 101.3 (CH$_2$), 105.7 (CH), 108.5 (CH), 122.5 (CH), 123.2 (CH), 124.6 (CH), 130.8 (C), 138.7 (CH), 140.9 (CH) 148.2 (C), 148.2 (C), 166.0 (C) MS m/z (%): 301 (M$^+$94), 202 (18) 201 (73), 174 (40), 173 (100), 172 (31), 171 (15) 143 (24), 115 (63) IR (KBr): ν$_{max}$ (carbonyl group) 1641 m.p. 149.5°–149.8° C. (Lit m.p. 139°–141° C.)$^4$, yield 50.1%

5-E,E-piperinoylmethylamine (RV-A07)

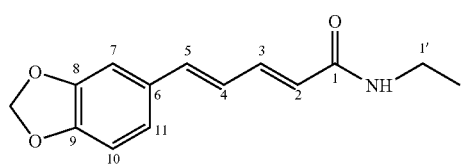

$^1$H-NMR (CDCl$_3$) δ: 5.91 (d, 1H, J=14.8, CH=CH—CH=CH), 7.36 (d,d, 1H, J=10.7, 14.8, CH=CH—CH=CH), 6.66 (d,d, 1H, J=15.4, 10.6, CH=CH—CH=CH), 6.77 (d, 1H, J=15.4 CH=CH—CH=CH), 6.97 (d,1H J=1.5, Ar-7H), 6.77 (d,1H J=8.0, Ar-10H), 6.88 (d, d, 1H J=1.6, 8.0 Ar-11H), 5.97 (s, 2H, O—CH$_2$—O), 2.91 (t, 3H, CH$_3$), 5.61 (br, NH) $^{13}$C-NMR (CDCl$_3$): 26.9 (CH$_3$), 101.7 (CH$_2$), 106.1 (CH), 108.9 (CH), 123.0 (CH), 123.3 (CH), 125.0 (CH), 131.2 (C), 139.2 (CH), 141.4 (CH), 148.6 (C), 148.6 (C), 167.2 (C) MS m/z (%): 231 (M$^+$89), 201 (42), 173 (67), 172 (32), 171 (17), 143 (27), 116 (21) 115 (100), 89 (12) m.p. 181.1°–182.4° C. (Lit m.p. 186° C.)$^5$, yield 48.2%

5-E,E-piperinoylethylamine (RV-A08)

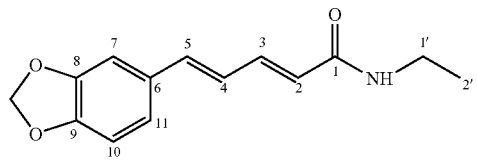

$^1$H-NMR (CD$_3$OD) δ: 6.14 (d, 1H, J=15.0, CH=CH—CH=CH), 7.37 (d,d, 1H, J=10.2, 15.0, CH=CH—CH=CH), 6.93 (d,d, 1H, J=15.7, 10.6, CH=CH—CH=CH), 6.87 (d, 1H, J=15.7 CH=CH—CH=CH), 6.97 (d,1H J=1.5, Ar-7H), 6.77 (d,1H J=8.0, Ar-10H), 6.88 (d, d, 1H J=1.6, 8.0 Ar-11H), 5.97 (s, 2H, O—CH$_2$—O), 3.39 (m, 2H, J=6.2, CH$_2$), 1.22 (t, 3H, J=6.1, CH$_3$), $^{13}$C-NMR (CDCl$_3$): 14.7 (CH$_3$), 36.9 (CH$_2$), 103.2 (CH$_2$), 107.2 (CH), 109.8 (CH), 121.2 (CH), 124.9 (CH), 125.9 (CH), 132.4 (C), 142.9 (CH), 145.2 (CH), 150.2 (C), 150.6 (C), 170 (C) MS m/z (%): 245 (M$^+$78), 218 (34), 201 (71), 200 (49), 174 (64), 173 (80), 172 (76), 171 (65), 143 (75), 116 (68), 115 (100) m.p. 158.5°–159.9° C. (Lit m.p. 162°–164° C.)$^4$, yield 45.6%

5-E,E-piperinoylisopropylamine (RV-A09)

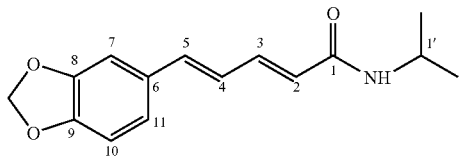

$^1$H-NMR (CDCl$_3$) δ: 5.87 (d, 1H, J=14.8, CH=CH—CH=CH), 7.36 (d,d, 1H, J=10.7, 14.8, CH=CH—CH=CH), 6.66 (d,d, 1H, J=15.4, 10.6, CH=CH—CH=CH), 6.76 (d, 1H, J=15.2 CH=CH—CH=CH), 6.97 (d,1H J=1.6, Ar-7H), 6.77 (d,1H J=8.0, Ar-10H), 6.88 (d,d, 1H J=1.6, 8.0 Ar-11H), 5.97 (s, 2H, O—CH$_2$—O), 4.15 (m, 1H, J=6.6, CH), 5.36 (d, 1H, J=7.3 NH), 1.19 (d, 6H, J=6.6, (CH$_3$)$_2$) $^{13}$C-NMR (CDCl$_3$): 23.2 (CH$_3$)$_2$, 41.9 (CH), 101.9 (CH$_2$), 106.4 (CH), 108.9 (CH), 123.0 (CH), 123.8 (CH), 124.1 (CH), 131.3 (C), 140.2 (CH), 141.2 (CH), 148.8 (C), 148.6 (C) 165.6 (C) MS m/z (%): 259 (M$^+$80), 201 (62), 174 (34), 173 (74), 172 (31), 171 (15), 143 (30), 116 (16), 115 (100) m.p. 169°–169.4° C. (Lit m.p. 171°–173° C.)$^4$, yield 52%

5-E,E-piperinoyl cyclohexylamine (RV-A10)

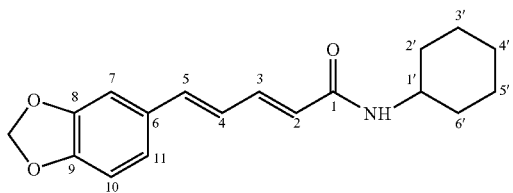

$^1$H-NMR (CDCl$_3$) δ: 5.93 (d, 1H, J=14.8, CH=CH—CH=CH), 7.35 (d,d, 1H, J=10.6, 14.8, CH=CH—CH=CH), 6.66 (d,d, 1H, J=15.3, 10.6, CH=CH—CH=CH), 6.76 (d, 1H, J=15.4 CH=CH—CH=CH), 6.96 (d,1H J=1.6, Ar-7H), 6.76 (d,1H J=8.0, Ar-10H), 6.87 (d,d, 1H J=1.6, 8.0 Ar-11H), 5.97 (s, 2H, O—CH$_2$—O), 3.87 (m, 1H, CH (cyclohexyl) 1.99 (m, 2H, CH$_2$(cyclohexyl)) 1.65 (m, 4H, CH$_2$—CH$_2$(cyclohexyl) 1.39 (m, 2H, CH$_2$ (cyclohexyl)) 1.18 (m, 2H, CH$_2$(cyclohexyl)) 5.48 (d, J=8.0 NH)

$^{13}$C-NMR (CDCl$_3$): 25.3 ((CH$_2$)$_2$), 25.9 (CH$_2$), 33.6 ((CH$_2$)$_2$), 48.6 (CH), 101.3 (CH$_2$), 101.7 (CH), 106.1 (CH), 108.9 (CH), 123.0 (CH), 124.0 (CH), 125.1 (CH), 131.3 (C), 139.0 (CH), 141.2 (CH) 148.5 (C), 148.5 (C), 165.5 (C) MS m/z (%): 299(M$^+$56), 259 (48) 216 (33), 201 (60), 174 (33), 173 (61), 172 (18), 171 (16) 143 (17), 115 (100) m.p. 196.4°–197.3° C. (Lit m.p. 199°–200° C.)$^4$, yield 57.4%

5-E,E-piperinoylbutylamine (RV-A11)

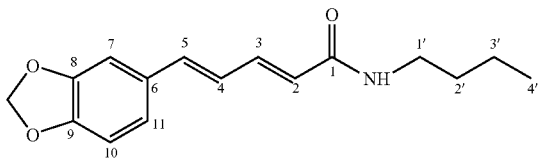

¹H-NMR (CDCl₃) δ: 5.97 (d, 1H, J=14.8, CH═CH—CH═CH), 7.35 (d,d, 1H, J=10.7, 14.8, CH═CH—CH═CH), 6.66 (d,d, 1H, J=15.4, 10.6, CH═CH—CH═CH), 6.76 (d,1H, J=15.4 CH═CH—CH═CH), 6.97 (d,1H J=1.6, Ar-7H), 6.77 (d,1H J=8.0, Ar-10H), 6.89 (d,d, 1H J=1.5, 8.0 Ar-11H), 5.97 (s, 2H, O—CH₂—O), 3.36 (q, 2H, CH₂—CH₂—CH₂—) 1.54 (m, 2H, CH₂—CH₂—CH₂) 1.39 (m, 6H, CH₂—CH₂—CH₂) 0.93 (t, 3H, CH₃), 5.47 (br, NH) ¹³C-NMR (CDCl₃): 14.2 (CH₃), 20.5 (CH₂), 32.2 (CH₂), 39.8 (CH₂), 101.7 (CH₂), 106.1 (CH), 108.9 (CH), 123.0 (CH), 123.6 (CH), 125.0 (CH), 131.3 (C), 139.2 (CH), 141.3 (CH) 148.6 (C), 148.6 (C), 166.4 (C) m.p. 144.2°–145.6° C. (Lit m.p. 144°–145° C.)⁴, yield 38.4%

References

[1] Chatterjee, A., and Dutta, C. P. (1967). Alkaloids of *Piper longuim* Linn-I Structure and synthesis of piperlongumine and piperlonguminine, Tetrahedron, 23, 1769–1781.
[2] Nokio Nakumara, Fumiyuki Kiuchi, and Yoshisuke Tsuda (1988). Infrared spectra of conjugated amides: Reassignment of the C═O and C═C absorptions: Chemical and Pharmaceutical Bulletin, 36, 2647–2651.
[3] H. Oediger and A. Schulze (Bayer AG), (1979), Deutsche Auslegeschrift 2757 483
[4] Paula, Vanderlucia F. de; A Barbosa, Luiz C. de; Demuner, Antonio J.; Pilo-Veloso, Dorila; Picanco, Marcelo C. (2000) Pest Management Science 56, 2, 168–174.
[5] Gokale et al., (1948) Journal of University Bombay Science 16/5A 32–35

3. Synthesis of Ester Derivatives of Piperinic Acid 3.1 Preparation of Piperinic Acid (RV-A00)

As described above.

3.2 Synthesis of 5-E,E-piperinic acid methyl ester (RV-AB1)

A mixture of piperinic acid (300 mg, 0.0014 mole, 1 eq) and triethylamine (0.39 ml, 0.0028 mole, 2 eq) in dichloromethane (50 ml) was stirred for 15 min at 0° C. To this mixture methanesulfonyl chloride (0.16 ml, 0.0021 mole, 1.5 eq) was added and stirred for further 30 min at 0° C. Methanol in excess (10 ml) was added to the mixture and stirred for 1 h at 0° C. and 1 h at room temperature. Dichloromethane (50 ml) was added to the mixture which was then washed with water (3×100 ml), 5% NaHCO₃ (3×100 ml) and water (3×100 ml). The organic fraction was dried over anhydrous sodium sulphate, filtered and rotary evaporated to yield a yellowish solid residue. Recrystallisation from ethyl acetate/petroleum spirit yielded ester (180 mg, 56.2% yield). m.p. 142.9°–143° C. (Lit m.p. 140° C.)⁶

3.3 Synthesis of Other Esters of Piperinic Acid.

They were synthesised as described in section 3.2, replacing methanol (10 ml) ethanol (10 ml), isopropanol, butanol or propanol (15 ml).

5-E,E-piperinic acid methyl ester (RV-AB1)

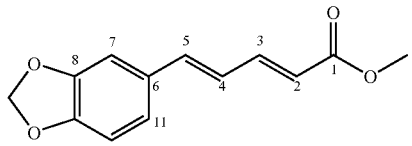

¹H-NMR (CDCl₃) δ: 5.94 (d, 1H, J=15.2, CH═CH—CH═CH), 7.41 (d,d, 1H, J=10.8, 15.2, CH═CH—CH═CH), 6.70 (d,d, 1H, J=15.4, 10.8, CH═CH—CH═CH), 6.81 (d, 1H, J=15.7 CH═CH—CH═CH), 6.99 (d,1H J=1.6, Ar-7H), 6.79 (d,1H J=8.1, Ar-10H), 6.91 (d,d, 1H J=1.5, 8.1 Ar-11H), 5.98 (s, 2H, O—CH₂—O), 3.57 (t, 3H, br, OCH₃,J=4.7) ¹³C-NMR (CDCl₃) δ: 51.5 (CH₃), 101.8 (CH₂), 106.2 (CH) 108.9 (CH), 120.0 (CH), 123.4 (CH) 124.7 (CH), 130.8 (CH), 140.9 (C), 145.5 (CH), 148.6 (C), 148.9 (C), 168.9 (C) MS m/z (%): 232 (M⁺ 69), 201 (19), 174 (12), 173 (100), 172 (39), 171 (12) 143 (33), 116 (11), 115 (53) 101 (15), 100 (12)

5-E,E-piperinic acid ethyl ester (RV-AB2)

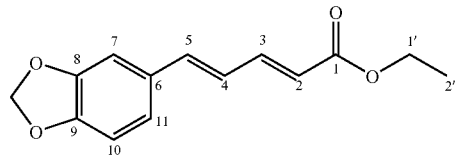

¹H-NMR (CDCl₃) δ: 5.94 (d, 1H, J=15.2, CH═CH—CH═CH), 7.41 (d,d, 1H, J=10.8, 15.3, CH═CH—CH═CH), 6.70 (d,d, 1H, J=15.4, 10.8, CH═CH—CH═CH), 6.81 (d, 1H, J=15.5 CH═CH—CH═CH), 6.99 (d,1H J=1.6, Ar-7H), 6.78 (d,1H J=8.1, Ar-10H), 6.91 (d,d, 1H J=1.6, 8.1 Ar-11H), 5.98 (s, 2H, O—CH₂—O), 4.22 (q, 2H, OCH₂ J=7.2), 1.31 (t, 3H, CH₃ J=7.2) ¹³C-NMR (CDCl₃): 14.7(CH₃), 60.7(CH₂), 101.6 (CH₂), 106.3 (CH) 108.9 (CH), 120.8 (CH), 123.3 (CH) 124.9 (CH), 131.0 (CH), 140.5 (CH), 145.1 (CH), 148.7 (C), 148.9 (C), 167.6 (C)

5-E,E-piperinic acid isopropyl ester (RV-AB4)

Physical data are not available for this compound.

5-E,E-piperinic acid propyl ester (RV-AB5)

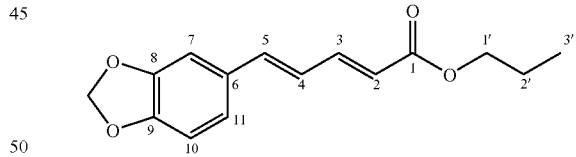

¹H-NMR (CDCl₃) δ: 5.94 (d, 1H, J=15.2, CH═CH—CH═CH), 7.41 (d,d, 1H, J=10.7, 15.2, CH═CH—CH═CH), 6.70 (d,d, 1H, J=15.4, 10.8, CH═CH—CH═CH), 6.76 (d, 1H, J=15.4 CH═CH—CH═CH), 6.99 (d,1H J=1.6, Ar-7H), 6.78 (d,1H J=8.1, Ar-10H), 6.91 (d,d, 1H J=1.5, 8.0 Ar-11H), 5.98 (s, 2H, O—CH₂—O), 4.12 (t, 2H, OCH₂ J=6.7) 1.69 (m, 2H, CH₂ J=7.3) 0.97 (t, 3H, CH₃ J=7.4) ¹³C-NMR (CDCl₃): 10.9 (CH₃), 22.5 (CH₂), 66.3 (CH₂), 101.8 (CH₂), 106.2 (CH) 108.9 (CH), 120.9 (CH), 123.3 (CH) 124.9 (CH), 131.0 (CH), 140.5 (CH), 145.1 (CH), 148.7 (C), 148.9 (C), 167.7 (C) MS m/z (%): 260 (M⁺ 59), 201 (26), 174 (18), 173 (100), 172 (39), 171 (14) 143 (34), 116 (16), 115 (73), 100 (12) m.p. 119°–120° C.

References

[6] Avijit Banerjee, Tapasree Ghosal, and Aditi Kacharya. (1984). Indian Journal of Chemistry, 23B, 546–549.

5-E,E-piperinic acid butyl ester (RV-AB6)

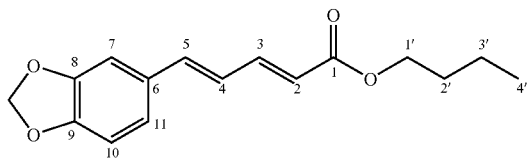

¹H-NMR (CDCl₃) δ: 5.94 (d, 1H, J=15.2, CH═CH—CH═CH), 7.40 (d,d, 1H, J=10.7, 15.3, CH═CH—CH═CH), 6.70 (d,d, 1H, J=15.4, 10.8, CH═CH—CH═CH), 6.76 (d, 1H, J=15.4 CH═CH—CH═CH), 6.99 (d,1H J=1.6, Ar-7H), 6.78 (d,1H J=8.0, Ar-10H), 6.91 (d,d, 1H J=1.5, 8.0 Ar-11H), 5.98 (s, 2H, O—CH₂—O), 4.12 (t, 2H, OCH₂ J=6.7) 1.69 (m, 2H, CH₂ J=7.3) 1.69 (m, 2H, CH₂ J=7.6), 0.95 (t, 3H, CH₃ J=7.5) MS m/z (%): 274 (M⁺ 50), 201 (15), 174 (14), 173 (100), 172 (30), 171 (14) 143 (21), 115 (55)
Obtained as an Oil.

4. Synthesis of amide derivatives of 3,4-methylenedioxycinnamic acid

These 3,4-methylenedioxycinnamide derivatives were synthesised as described in Section 2.2, but using 3,4-methylenedioxycinnamic acid (500 mg) as the starting acid and reducing the proportion of triethylamine to 1.5 equivalent with respect to the starting acid. Also, in the first stage, the reaction mixture was stirred for 2 hours, instead of 30 minutes, again at 0° C.

1-(3-trans-benzo-1,3-dioxol-5-ylacryloyl)piperidine (RV-B01)

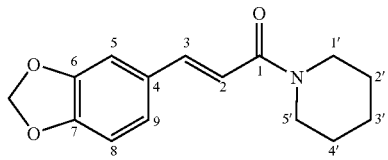

¹H-NMR (CDCl₃) δ: 7.56 (d, 1H, J=15.3, CH═CH), 6.73 (d, 1H, J=15.3, CH═CH—), 7.03 (d,1H J=1.5, Ar-7H), 6.79 (d,1H, J=8.0, Ar-8H), 6.99 (d,d, 1H J=1.6, 8.0 Ar-9H), 5.98 (s, 2H, O—CH₂—O), 3.57 (br, 2H, CH₂—N—CH₂), 3.65 (br, 2H, CH₂—N—CH₂(piperidine)), 1.65 (m, 6H, CH₂—CH₂—CH₂-(piperidine)) ¹³C-NMR (CDCl₃): 24.8 (CH₂), 25.6 (CH₂), 26.7 (CH₂), 43.3 (CH₂), 46.9 (CH₂), 101.3 (CH₂), 106.7 (CH), 108.4 (CH), 115.6 (CH), 123.5 (CH), 129.9 (C), 141.9 (CH) 148.1 (CH), 148.8 (C), 165.4 (C) m.p. 80.1°–82° C. (Lit m.p. 80°–82° C.)⁷, yield 49.2%

1-(3-trans-benzo-1,3-dioxol-5-ylacryloyl)pyrrolidine (RV-B02)

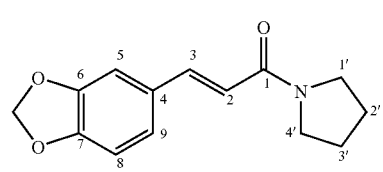

¹H-NMR (CDCl₃) δ: 7.60 (d, 1H, J=15.2, CH═CH), 6.73 (d, 1H, J=15.3, CH═CH—), 7.04 (d,1H J=1.5, Ar-7H), 6.80 (d,1H J=8.0, Ar-8H), 7.01 (d,d, 1H J=1.5, 8.0 Ar-9H), 5.99 (s, 2H, O—CH₂—O), 3.61 (br, 2H, CH₂—N—CH₂ (pyrrolidine)), 3.57 (br, 2H, CH₂—N—CH₂(pyrrolidine)), 1.99 (4H, CH₂—CH₂(pyrrolidine)), ¹³C-NMR (CDCl₃): 24.3 (CH₂), 26.1 (CH₂) 46.0 (CH₂), 46.5 (CH₂), 101.4 (CH₂), 106.4 (CH), 108.5 (CH), 116.8 (CH), 123.8 (CH), 129.7 (C), 141.0 (CH) 148.1 (C), 148.9 (C), 164.8 (C) MS m/z (%): 245 (M⁺ 62), 176 (41) 175 (100) 145 (36), 117 (11), 89 (14). m.p. 152.5°–153° C., yield 44.1%

1-(3-trans-benzo-1,3-dioxol-5-ylacryloyl)morpholine (RV-B03)

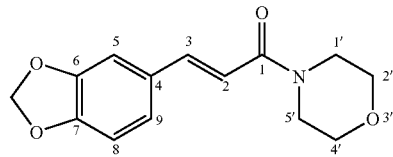

¹H-NMR (CDCl₃) δ: 7.61 (d, 1H, J=15.3, CH═CH), 6.73 (d, 1H, J=15.3, CH═CH—), 7.03 (d,1H J=1.4, Ar-7H), 6.80 (d,1H J=8.0, Ar-8H), 7.01 (d,d, 1H J=1.4, 8.0 Ar-9H), 5.99 (s, 2H, O—CH₂—O), 3.72 (br, 4H, CH₂—N—CH₂ (morpholine)), 3.67 (br, 4H, CH₂—O—CH₂(morpholine)), ¹³C-NMR (CDCl₃): 42.6 (CH₂), 46.2 (CH₂), 66.8 (CH₂), 46.5 (CH₂), 101.4 (CH₂), 106.3 (CH), 108.5 (CH), 114.4 (CH), 123.9 (CH), 129.5 (CH), 143.0 (CH) 148.2 (C), 148.9 (C), 149.1 (C), 165.6 (C) MS m/z (%): 261 (M⁺ 60), 176 (24) 175 (100) 145 (30), 117 (10), 89 (11). m.p. 160°–160.3° C., yield 50.1%

5. Synthesis of 3-trans-benzo-1,3-dioxol-5-ylacrylic acid methyl ester (RV-BB1)

To 3,4-methylenedioxycinnamic acid (2 g, 0.01 mol, 1 eq) methanol (4 ml, 10 eq) was added. Sulphuric acid (0.2 ml) was added and refluxed overnight. The solvent was rotary evaporated to yield solid residue. This residue was dissolved in ether and washed with water (2×100 ml) and 5% NaHCO₃ (3×100 ml) and with water (2×100 ml). The organic fraction was dried over anhydrous sodium sulphate and rotary evaporated to yield white solid. Recrystallisation from ethyl acetate/petroleum spirit yielded crystals (69.4% yield)

m.p. 133.7°–134.2° C. (Lit m.p.134° C.)⁸

3-trans-benzo-1,3-dioxol-5-ylacrylic acid methyl ester (RV-BB1)

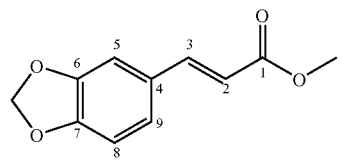

¹H-NMR (CDCl₃) δ: 7.59 (d, 1H, J=15.9, CH═CH), 6.26 (d, 1H, J=15.9, CH═CH—), 7.03 (d,1H J=1.5, Ar-7H), 6.81 (d,1H J=8.0, Ar-8H), 7.01 (d,d, 1H J=1.5, 8.0 Ar-9H), 6.00 (s, 2H, O—CH₂—O), 3.79 (s, 3H, OCH₃) ¹³C-NMR (CDCl₃): 51.6 (CH₃), 101.5 (t CH₂), 106.5 (CH), 108.5 (CH), 115.7 (CH), 124.4 (CH), 128.8 (CH), 144.5 (CH) 148.3 (C), 148.6 (C), 148.2 (C), 167.6 (C) MS m/z (%): 206(M⁺ 100), 175 (68) 175 (100) 145 (27), 117 (10), 89 (11).

References

⁷H. Staudinger and H. Schneider. (1923). Chem. Ber. 56, 699.

⁸Takemoto et al. (1985). Chemical and Pharmaceutical Bulletin 23, 1161.

6. Synthesis of Tetrahydropiperine (RV-C02)

Piperine (2 g, 7 mmol) was hydrogenated in ethanol (50 ml) over 5% Pd-C under a pressure of hydrogen at 10 psi for 30 mins to give tetrahydropiperine (1.59 g, 78% yield) as an oil².

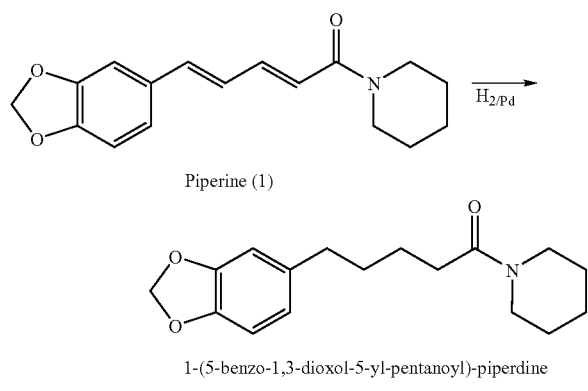

Piperine (1)

1-(5-benzo-1,3-dioxol-5-yl-pentanoyl)-piperdine

Tetrahydropiperine (RV-C02)

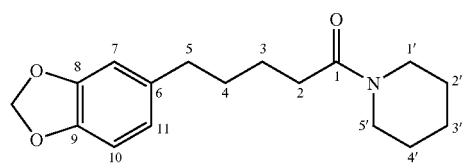

¹H-NMR (CDCl₃) δ: 2.55 (t, 4H, J=7.0 CH₂_CH₂_CH₂_CH₂), 2.32 (t, 4H, J=7.0 CH₂CH₂_CH₂_CH₂) 6.66 (d,1H J=1.3, Ar-7H), 6.70 (d,1H J=8.0, Ar-10H), 6.61 (d,d, 1H J=1.2, 8.0 Ar-11H), 5.89 (s, 2H, O—CH₂—O), 3.53 (t, 2H, N—CH₂ (piperidine)) 3.35 (t, 2H, N—CH₂ (piperidine)) 1.63 (m, 2H, CH₂_CH₂_CH₂(piperidine)) 1.54 (m, 2H, CH₂_CH₂_CH₂(piperidine)) ¹³C-NMR (CDCl₃): 24.5 (CH₂), 24.9 (CH₂), 25.5 (CH₂), 26.5 (CH₂), 31.4 (CH₂), 33.2 (CH₂), 35.4 (CH₂), 42.5 (CH₂), 46.6 (CH₂), 100.7 (CH₂), 108.0 (CH), 108.8 (CH), 109.0 (CH), 121.0 (C), 145.4 (C) 147.4 (C), 171.1 (C) MS m/z (%): 289 (M⁺ 71), 204 (31), 154 (23), 148 (22), 141 (23), 140 (38), 135 (28) 127 (100), 112 (23), 86 (12), 84 (24), 70 (10), 36 (11)

Preparation of 5-(3,4-methylenedioxy Phenyl)-pentanoic acid cyclohexyl amide (RV-C04)

To 5-(3,4-methylenedioxy phenyl)-2E,4E-pentadienoic acid cyclohexyl amide (300 mg) was added 5% Pd/C (30 mg) and hydrogenated the contents at 30 psi for 1 hr. The solution was filtered and rotary evaporated to yield a white solid. Recrystallisation from ethylacetate and petroleum spirit yielded pure white crystals (255 mg, yield 84%). m.p. 145.4° C.–146.3° C.

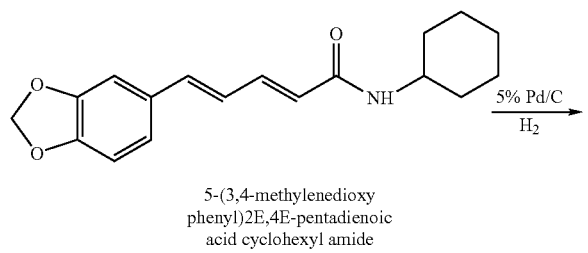

5-(3,4-methylenedioxy phenyl)2E,4E-pentadienoic acid cyclohexyl amide

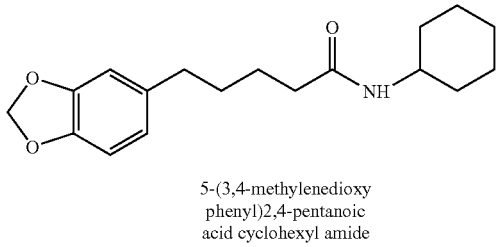

5-(3,4-methylenedioxy phenyl)2,4-pentanoic acid cyclohexyl amide

Preparation of 7-(3,4-methylenedioxy Phenyl)-heptanoic acid piperidine amide (RV-C05)

To 7-(3,4-methylenedioxy phenyl)-2E,4E,6E-heptatrienoic acid piperidine amide (150 mg, 0.06 mmole) was added 5% Pd/C (15 mg) and hydrogenated the contents at 30 psi for 30 min to give 7-(3,4-methylenedioxy phenyl)-heptanoic acid piperidine amide as an oil.

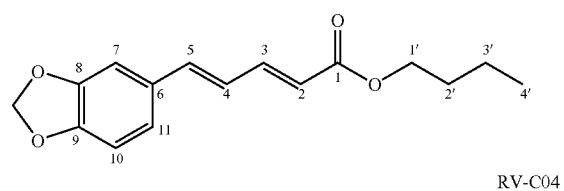

RV-C04

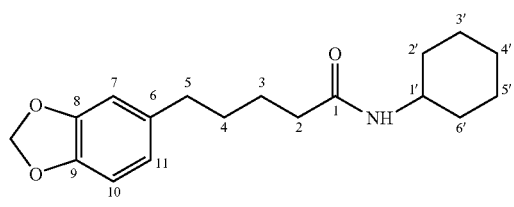

¹H-NMR (CDCl₃) δ: 6.65 (d,1H J=1.6, Ar-7-H), 6.71 (d,1H J=7.8, Ar-10-H), 6.60 (d,d, 1H J=1.6, 8.0 Ar-11-H), 5.90 (s, 2H, O—CH₂—O), 5.43 (s, 1H, NH), 2.53 (t, 2H, J=7.7 (CH₂—CH₂_CH₂CH₂)) 2.14 (t, 2H, J=7.7 ((CH₂_CH₂_CH₂_CH₂)) 1.62–1.91 (m, 10H, CH₂—CH₂_CH₂_CH₂_CH₂_CH₂_CH₂ (cyclohexyl amide) 1.07–1.30 (m, 4H, CH₂_CH_CH₂ (cyclohexylamide)) ¹³C-NMR (CDCl₃): 25.3 ((CH₂)₂), 25.7 (CH₂), 25.9 (CH₂), 31.3 (CH₂), 31.7 (CH₂), 33.6 (CH₂), 35.8 (CH₂), 37.3 (CH₂), 48.4 (CH), 101.1 (CH₂), 108.4 (CH), 109.2 (CH), 121.4 (CH), 136.4 (C), 145.8 (C), 147.8 (C), 172.2 (C), MS m/z (%): 303 (M⁺ 98), 204 (72), 176 (13), 168 (16), 162 (12) 161 (14), 154 (27), 148 (66), 141 (61) 135 (100) 74 (24) 60 (60)

RV-C05

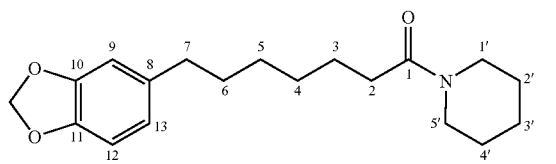

¹H-NMR (CDCl₃) δ: 6.66 (d,1H J=1.5, Ar-7-H), 6.71 (d,1H J=7.8, Ar-10-H), 6.60 (d,d, 1H J=1.6, 8.0 Ar-11-H), 5.90 (s, 2H, O—CH₂—O), 3.53 (t, 2H, J=5.4 CH₂_N_CH₂) 3.37 (t, 2H, J=5.7, (CH₂—N—CH₂) 2.51 (t, 2H, J=7.7 (CH₂—CH₂_CH₂_CH₂_CH₂_CH₂)) 2.33(t, 2H, J=7.7 ((CH₂—CH₂_CH₂_CH₂_CH₂_CH₂)) 1.52–1.65 (m, 10H, hydrocarbon CH₂, CH₂, CH₂—CH₂—CH₂ (Piperidine)) 1.34 (m, 4H, CH₂ CH₂) ¹³C-NMR (CDCl₃): 24.9 (CH₂), 25.8 (CH$_2$), 25.9 (CH$_2$), 26.9 (CH$_2$), 29.3 (CH$_2$), 29.7 (CH$_2$), 31.3 (CH$_2$), 31.9 (CH$_2$), 33.8 (CH$_2$), 42.9 (CH$_2$), 47.1 (CH$_2$), 101.8 (CH$_2$), 108.4 (CH), 109.2 (CH), 121.4 (CH), 137.0 (C), 145.7 (C), 147.8 (C), 171.8 (C), MS m/z (%): 317 (M$^+$ 78), 232 (11), 204 (10), 183 (30), 182 (15), 154 (21) 148 (43), 141 (41), 127 (100), 112 (43), 85 (49) Yield 51.2%

7. Synthesis of 3-benzo-1,3-dioxol-5-ylpropionic acid piperidide 7.1 Synthesis of 3-benzo-1,3-dioxol-5-ylpropionic acid 3-benzo-1,3-dioxol-5-ylacrylic acid (2 g) was hydrogenated in ethanol (50 ml) over 5% Pd-C under a pressure of hydrogen at 10 psi for 40 mins to give 3-benzo-1,3-dioxol-5-ylpropionic acid (1.67 g, 80% yield) as a solid, m.p. 86.1°–88.3° C. (Lit m.p. 87–88° C.)[10]

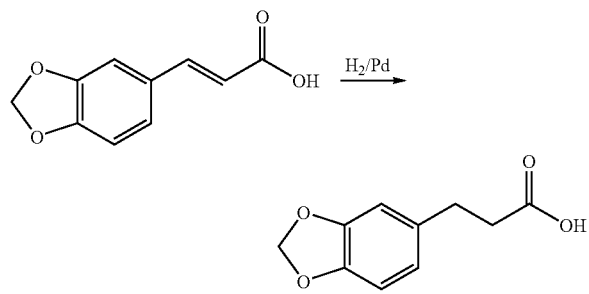

7.2 Synthesis of 3-benzo-1,3-dioxol-5-ylpropionic acid piperidide (RV-C03)

The method was adapted from that reported for piperlonguminine (section 2.2) but utilising 3-benzo-1,3-dioxol-5-ylpropionic acid and piperidine as the acid and amine components respectively. A mixture of 3-benzo-1,3-dioxol-5-ylpropionic acid (200 mg, 0.0026 mole, 1 eq) and triethylamine (0.27 ml, 0.002 mole, 2 eq) in dichloromethane (50 ml) was stirred for 15 min at 0° C. To this mixture methanesulfonyl chloride (0.11 ml, 0.0015 mole, 1.5 eq) was added and stirred for further 30 min at 0° C. Piperidine (0.15 ml, 0.0015 mole, 1.5 eq) was added to the mixture and stirred for 1 h at 0° C. and 1 h at room temperature. Dichloromethane (50 ml) was added to the mixture which was then washed with 5% HCl (3×100 ml), saturated aqueous NaHCO$_3$ (3×100 ml) and water (3×100 ml). The organic fraction was dried over anhydrous sodium sulphate, filtered and rotary evaporated to yield brown oil (65% yield).

3-benzo-1,3-dioxol-5-ylpropionic acid piperidide (RV-C03)

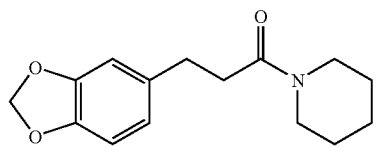

$^1$H-NMR (CDCl$_3$) δ: 2.87 (t, 2H, J=7.3 CH$_2$), 2.57 (t, 2H, J=7.0 CH$_2$.CH$_2$) 6.70 (d,1H J=1.5, Ar-7H), 6.72 (d,1H J=8.0, Ar-10H), 6.66 (d,d, 1H J=1.2, 8.0 Ar-11H), 5.90 (s, 2H, O—CH$_2$—O), 3.55 (t, 2H, N—CH$_2$-(piperidine)) 3.34 (t, 2H, N—CH$_2$ (piperidine)) 1.62 (m, 2H, CH$_2$.CH$_2$.CH$_2$ (piperidine)) 1.49 (m, 2H, CH$_2$.CH$_2$.CH$_2$(piperidine)) $^{13}$C-NMR (CDCl$_3$): 25.7 (CH$_2$), 25.9 (CH$_2$), 26.6 (CH$_2$), 31.7 (CH$_2$), 35.8 (CH$_2$), 43.1(CH$_2$), 47.1(CH$_2$), 101.2 (CH$_2$), 109.2 (CH), 109.3 (CH), 121.5 (CH), 135.6 (C), 146.2 (C) 148.0 (C), 170.8 (C)

References

[9]Biswanath Das., A. Kasinatham., and P. Madhusudhan. (1998). Regioselective reduction of αβ-double bond of some naturally occuring dienamides using NABH$_4$/I$_2$ system. Tetrahedron Letters 39, 677–678.

[10]Perkin, Robinson, (1907) Journal of Chemical Society 91, 1084

8 Synthesis of Amide Derivatives of Methoxy-Substituted Cinnamic Acid

A mixture of monomethoxycinnamic acid (200 mg, 0.89 mmol, 1 eq) and triethylamine (2.4 ml, 1.78 mmol, 2 eq) in dichloromethane (50 ml) was stirred for 15 min at 0° C. To this mixture methanesulfonyl chloride (1.02 ml, 1.33 mmol, 1.5 eq) was added and stirred for further 30 min at 0° C. Piperidine (0.23 ml, 1.33 mmol, 1.5 eq) was added to the mixture and stirred for 1 h at 0° C. and 1 h at room temperature. Then dichloromethane (50 ml) was added to the mixture, which was then washed with 5% HCl (3×100 ml), saturated aqueous NaHCO$_3$ (3×100 ml) and water (3×100 ml). The organic fraction was dried over anhydrous sodium sulphate, filtered and rotary evaporated to yield an oil. This oil was purified by chromatography on silica gel using ethyl acetate/petroleum spirit (2:8) as an eluant.

The piperidine amide of 3,4 dimethoxycinnamic acid was prepared in the same way utilising 200 mg of the acid.

1-(2-methoxy-cinnamoyl)-piperidine (RV-G01)

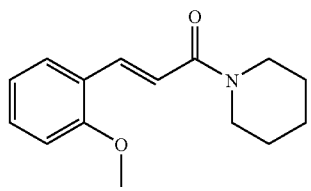

$^1$H-NMR (CDCl$_3$) δ: 7.56 (d, 1H, CH=CH), 7.29 (d, 1H, J=7.8 ArH), 7.12(d, 1H, J=7.6 ArH) 7.0 (d,d 1H, J=1.8 ArH) 6.86–6.90 (m, ArH), 6.88 (d, 1H, J=15.4 CH=CH), 3.58–3.66 (br, 4H, CH$_2$—N—CH$_2$ (piperidine)) 1.56–1.71 (m, 6H, CH$_2$.CH$_2$.CH$_2$ (piperidine)) 3.83 (s, 3H, OCH$_3$) $^{13}$C-NMR (CDCl$_3$): 25.7 (CH$_2$), 26.0 (CH$_2$), 27.1 (CH$_2$), 43.7 (CH$_2$), 47.4(CH$_2$), 55.7(CH$_3$), 113.4 (CH), 115.3 (CH), 118.5 (CH), 120.6 (CH), 130.1 (CH), 142.4 (CH), 137.3 (C), 160.2 (C), 165.6 (C) MS m/z (%): 245 (M$^+$ 28), 162 (22), 161 (100), 133 (20), 118 (24), 113 (14), 84 (51) yield 25.5%

1-(3-methoxy-cinnamoyl)piperidine (RV-G02)

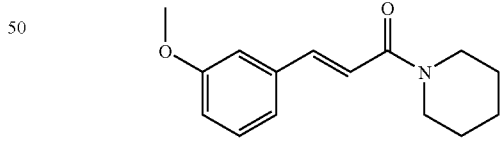

$^1$H-NMR (CDCl$_3$) δ: 7.60 (d, 1H, J=15.4, CH=CH), 7.29 (d, 1H, J=7.8 ArH), 7.12 (d, 1H, J=7.6 ArH) 7.0 (d,d 1H, J=1.8 ArH) 6.86–6.90 (m, ArH), 6.88 (d, 1H, J=15.4 CH=CH), 3.58–3.66 (br, 4H, CH$_2$—N—CH$_2$ (piperidine)) 1.56–1.71 (m, 6H, CH$_2$.CH$_2$ CH$_2$(piperidine)) 3.83 (s, 3H, OCH$_3$) $^{13}$C-NMR (CDCl$_3$): 25.7 (CH$_2$), 26.0 (CH$_2$), 27.1 (CH$_2$), 43.7 (CH$_2$), 47.4(CH$_2$), 55.7(CH$_3$), 113.4 (CH), 115.3 (CH), 118.5 (CH), 120.6 (CH), 130.1 (CH), 142.4 (CH), 137.3 (C), 160.2 (C), 165.6 (C) MS m/z (%): 245(M$^+$ 77), 162 (65), 161 (100), 133 (20), 118 (24), 113 (14), 84 (51) m.p. 68°–70° C., yield 31.4%

1-(4-methoxy-cinnamoyl)piperidine (RV-G03)

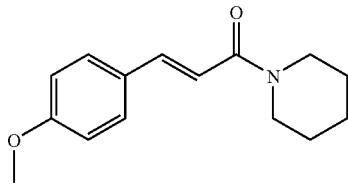

$^1$H-NMR (CDCl$_3$) δ: 7.61 (d, 1H, J=15.4, CH=CH), 7.47 (d, 2H, J=7.8 ArH), 6.87–6.90 (m,2H,ArH), 6.77 (d, 1H, J=15.4 CH=CH), 3.58–3.65 (br, 4H, CH$_2$—N—CH$_2$ (piperidine)) 1.52–1.69 (m, 6H, CH$_2$.CH$_2$.CH$_2$ (piperidine)) 3.82 (s, 3H, OCH$_3$) $^{13}$C-NMR (CDCl$_3$): 25.6 (CH$_2$), 26.0 (CH$_2$), 26.4 (CH$_2$), 43.7(CH$_2$), 47.4(CH$_2$), 55.7(CH$_3$), 114.5 (CH), 115.6 (CH), 118.5 (CH), 121.9 (CH), 129.6 (CH), 142.2 (CH), 132.8 (C), 161.0 (C), 166.0 (C) MS m/z (%): 245(M$^+$ 71), 162 (17), 161 (100), 133 (26), 118 (12), 113 (14), 84 (24), 77 (36)

1-(3,4-dimethoxycinnamoyl)piperidine (RV-G04)

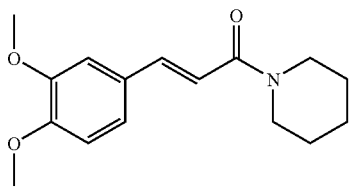

$^1$H-NMR (CDCl$_3$) 60 MHz δ: 7.61 (1H, CH=CH), 7.23 (1H, ArH), 6.98(1H, ArH) 6.82 (1H, J=1.8 ArH) 6.68 (1H, CH=CH), 3.58–3.65 (br, 4H, CH$_2$—N—CH$_2$ (piperidine)) 1.5–1.8 (6H, CH$_2$.CH$_2$.CH$_2$ (piperidine)) 3.91 (s, 6H, OCH$_3$)$_2$) MS m/z (%): 275 (M$^+$ 62), 192 (48), 191 (100), 161 (18), 118 (11), 84 (26), 77 (12), yield 42.3%

What is claimed is:

1. A method of treating a skin condition of a subject wherein the skin condition is selected from the group of conditions (a) vitiligo and (b) melanomas, which comprises administering to the subject an effective amount of a compound of formula (1)

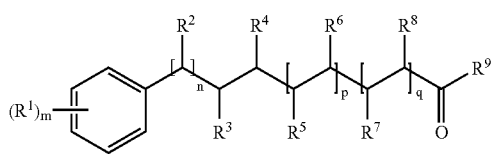

wherein n=0 or 1;
p is 0 or 1;
q is 0 or 1
when n=p=q=0, R$^3$ and R$^4$ represent hydrogen or together represent a carbon to carbon double bond;
when n=0 and one of p and q=1, R$^3$ and R$^4$ together and one of R$^5$ and R$^6$ together or R$^7$ and R$^8$ together represent carbon to carbon double bonds, R$^3$ and R$^4$ together represent a carbon to carbon double bond and R$^5$ and R$^6$ or R$^7$ and R$^8$ represent hydrogen atoms, R$^3$ and R$^4$ represent hydrogen and one of R$^5$ and R$^6$ together or R$^7$ and R$^8$ together represent carbon to carbon double bonds or R$^3$, R$^4$, R$^5$, R$^6$, R$^7$ and R$^8$ all represent hydrogen atoms; when n=0 and p=q=1, R$^3$ and R$^4$ together and one of R$^5$ and R$^6$ together or R$^7$ and R$^8$ together represent carbon to carbon double bonds the other of R$^5$, R$^6$, R$^7$ and R$^8$ representing hydrogen, R$^3$ and R$^4$ together represent a carbon to carbon double bond and R$^5$ and R$^6$ or R$^7$ and R$^8$ represent hydrogen atoms, R$^3$ and R$^4$ represent hydrogen and one of R$^5$ and R$^6$ together or R$^7$ and R$^8$ together represent carbon to carbon double bonds the other of R$^5$, R$^6$, R$^7$ and R$^8$ representing hydrogen, R$^3$ and R$^4$ together, R$^5$ and R$^6$ together and R$^7$ and R$^8$ together represent carbon to carbon double bonds or R$^3$, R$^4$, R$^5$, R$^6$, R$^7$ and R$^8$ all represent hydrogen atoms;
or optionally when n is 1 R$^2$ and R$^3$ together represent a carbon to carbon double bond and one or more of R$^4$ and R$^5$ together, R$^5$ and R$^6$ together, R$^6$ and R$^7$ together or R$^7$ and R$^8$ together represent a carbon to carbon double bond the other of R$^4$ to R$^8$ representing hydrogen;
m=1, 2 or 3;
when m=1, R$^1$ represents an alkoxy group having from 1 to 3 carbon atoms or a hydroxy group;
when m=2, each R$^1$ independently represents an alkoxy group having from 1 to 3 carbon atoms or the two R$^1$s together represent a 3',4'-methylenedioxy group;
when m=3, two R$^1$s together represent a 3',4'-methylenedioxy group and the other R$^1$ represents an alkoxy group having from 1 to 3 carbon atoms or a hydroxy group; R$^9$ represents a pyrrolidino, piperidino, 4-methylpiperidino or morpholino group, a N-monoalkylamino group of 4 to 6 carbon atoms, a N-monocycloalkylamino group of 4 to 7 carbon atoms, a 3',4'-methylenedioxy-substituted benzylamino or 2-phenethylamino group or R$^9$ represents an alkoxy group of 1 to 6 carbon atoms;
in any of its E, Z geometrically isomeric forms.

2. The method of claim 1, wherein the skin condition is a melanoma and the subject is a patient.

3. The method of claim 1, wherein the subject is a patient and the skin condition is treatable by stimulation of melanocyte proliferation.

4. The method of claim 1, wherein the skin condition is vitiligo.

5. The method of claim 1, wherein the compound is administered topically to the area of the skin to be treated.

6. The method of claim 1, wherein the compound of formula (1) is one in which:
n=0, one of p and q=1, R$^3$ and R$^4$ together and one of R$^5$ and R$^6$ together or R$^7$ and R$^8$ together represent the second bond of a carbon to carbon double bond the other of R$^5$, R$^6$, R$^7$ and R$^8$ representing hydrogen, m=2, the R$^1$ groups together represent 3',4'-methylenedioxy and R$^9$ represents a pyrrolidino, piperidino, morpholino, cyclohexylamino or isobutylamino group.

7. The method of claim 6, wherein the compound is of the E, E geometric configuration.

8. The method of claim 1, wherein the compound of formula (I) is one in which n is 0, one of p and q is 1, R$^3$, R$^4$, R$^5$, R$^6$, R$^7$ and R$^8$ represent hydrogen and R$^9$ is cyclohexylamino.

9. The method of claim 1, wherein the compound of formula (1) is piperine, being the E, E-isomer of the compound of formula (1) in which n=0, one of p or q=1, R$^3$ and R$^4$ together and one of R$^5$ and R$^6$ together or R$^7$ and R$^8$ together represent the second bond of a carbon to carbon double bond, the other of R$^5$, R$^6$, R$^7$ and R$^8$ representing hydrogen, m=2, the R$^1$ groups together represent 3',4'-methylenedioxy and R$^9$ represents piperidino, and the geometric configuration is E, E.

10. A method of treating a skin condition of a subject wherein the skin condition is selected from the group of conditions (a) vitiligo and (b) melanomas, which comprises administering to the subject an effective amount of a compound of formula (1)

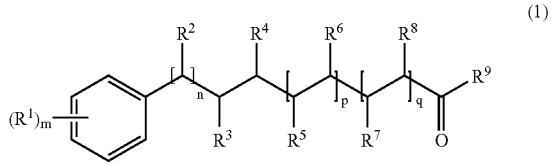

in which
- (a) n is 0, p and q are each 0 or 1, m is 2, the $R^1$s together represent a 3',4'-methylenedioxy group, $R^2$ and $R^3$, together with the carbon atoms to which they are attached form a carbon to carbon double bond and, when p and q are each 0 or 1, $R^5$ and $R^6$ and $R^7$ and $R^8$ together with the carbon atoms to which they are attached, form a carbon to carbon double bond and $R^9$ is piperidino, or
- (b) n is 0, one of p or q is 1 and (i) m is 3, the $R^1$s being 3',4'-methylenedioxy and 6'-methoxy or (ii) m is 2, the $R^1$s being 3'-hydroxy-4'-methoxy; or (iii) m is 1 and the $R^1$ is 4'-hydroxy; and $R^3$ to $R^9$ are as defined in case (a) above, or
- (c) n is 0, one of p and q is 1, $R^9$ is piperidino, pyrrolidino, isobutylamino or methoxy and all other symbols are as defined in case (a) above, or
- (d) n is 0, one of p and q is 1, $R^4$ and $R^5$ represent hydrogen atoms and either $R^2$ and $R^3$ also do or $R^2$ and $R^3$ together with the carbon atoms to which they are attached form a carbon to carbon double bond; and m, $R^1$ and $R^9$ are as defined in case (a) above;
- (e) n is 0, p=q=1 and $R^3$, $R^4$, $R^5$, $R^6$, $R^7$ and $R^8$ represent hydrogen;
- (f) n is 0, one of p and q is 1, $R^3$, $R^4$, $R^5$, $R^6$, $R^7$ and $R^8$ represent hydrogen and $R^9$ is cyclohexylamino; and in all of which cases (a) to (f) the molecule is in the E,E or all E geometric configuration or in case (a) when n is 1 may be in the Z,Z, Z,E or E,Z geometric configuration.

11. The method of claim 10, the skin condition is a melanoma and the subject is a patient.

12. The method of claim 10, wherein the subject is a patient and the skin condition is treatable by stimulation of melanocyte proliferation.

13. The method of claim 10, wherein the skin condition is vitiligo.

* * * * *